United States Patent [19]
Abe et al.

[11] Patent Number: 5,658,915
[45] Date of Patent: Aug. 19, 1997

[54] POLYELECTROLYTE COMPLEX ANTIBACTERIAL AGENT AND ANTIBACTERIAL MATERIAL

[75] Inventors: Koji Abe, Nagano; Mitsunao Tanaka, Tokyo; Satoshi Inaba, Tokyo; Masaharu Akimoto, Tokyo, all of Japan

[73] Assignee: Iatron Laboratories, Inc., Tokyo, Japan

[21] Appl. No.: 519,298

[22] Filed: Aug. 25, 1995

Related U.S. Application Data

[62] Division of Ser. No. 317,288, filed as PCT/JP91/01639, Nov. 28, 1991, Pat. No. 5,578,598.

[30] Foreign Application Priority Data

| Nov. 29, 1990 | [JP] | Japan | 2-325405 |
| Nov. 29, 1990 | [JP] | Japan | 2-325406 |
| Oct. 26, 1991 | [JP] | Japan | 3-306857 |
| Oct. 26, 1991 | [JP] | Japan | 3-306858 |

[51] Int. Cl.$^6$ .................... A61K 31/495
[52] U.S. Cl. .................... 514/255
[58] Field of Search ............ 514/255, 642, 514/643, 516

[56] References Cited

U.S. PATENT DOCUMENTS

| 4,104,466 | 8/1978 | Tsuchida et al. | 542/433 |
| 4,107,097 | 8/1978 | Seita et al. | 521/32 |
| 4,113,709 | 9/1978 | Quinian | 424/78 |
| 4,339,430 | 7/1982 | Gaffar | 424/54 |
| 4,361,548 | 11/1982 | Smith et al. | 424/78 |
| 4,501,834 | 2/1985 | Su | 524/28 |
| 4,729,792 | 3/1988 | Seitz | 106/21 |
| 5,260,002 | 11/1993 | Wang | 264/4.1 |
| 5,578,598 | 11/1996 | Abe et al. | 514/255 |

*Primary Examiner*—John W. Rollins
*Attorney, Agent, or Firm*—Burgess, Ryan & Wayne

[57] ABSTRACT

An antibacterial agent characterized by containing a polyelectrolyte complex prepared by reacting a cationic polymer containing $N^+$ atoms in repeating units thereof and an anionic polymer containing $-COO^-$, $-SO_3^-$, or $-PO_3^-$ groups in repeating units thereof, and an antibacterial material carrying the above polyelectrolyte complex on a carrier.

6 Claims, No Drawings

POLYELECTROLYTE COMPLEX ANTIBACTERIAL AGENT AND ANTIBACTERIAL MATERIAL

This is a division, of application Ser. No. 08/317,288, filed as PCT/JP91/01639 Nov. 28, 1991, now U.S. Pat. No. 5,578,598.

TECHNICAL FIELD

The present invention relates to an antibacterial agent comprising a polyelectrolyte complex and an antibacterial material carrying the polyelectrolyte complex.

BACKGROUND ART

Organic compounds having a positive charge are known to exhibit antibacterial properties, regardless of whether they are low molecular weight compounds or high molecular weight compounds. The application technology utilizing such properties has spread widely from the medical field to general clothing. For example, quaternary ammonium compounds such as benzalkonium chloride or the like are soluble in water, and so are in themselves used as sterilizing or disinfecting solutions. Conversely, however, since they are soluble in water, the range of usage as antibacterial agents is limited.

Further, anionic groups are introduced to the surface of synthetic polymer articles and then treatment with quaternary ammonium bases is performed so as to obtain a material maintaining an antibacterial property over a sustained long term period. The resulting material is used as a filter material for air filters and dialysis. This technique is also applied to textile materials, and utilized for clothing having antibacterial properties and agents for protecting wound.

As a means of introducing quaternary ammonium to the surface of a polymer material to obtain a material exhibiting sustained antibacterial properties, for example, Japanese Published Unexamined Patent Application No. 54-86584 describes a method for bringing a polymer obtained by polymerizing an acidic-group-containing monomer into contact with an aqueous solution of a quaternary ammonium base. Further, Japanese Published Unexamined Patent Application No. 59-164342 discloses a method for introducing an anionic-group-containing vinyl monomer to the surface of a synthetic polymer article by graft polymerization or the like, and then treating by a quaternary ammonium base.

In the conventional methods, however, the rate of introduction of the quaternary ammonium base for manifesting the antibacterial property was not necessarily sufficient and a satisfactory sustenance could not be obtained. Further, the process of production was also complicated.

The present inventors engaged in intensive research with the object of obtaining a material having a sustained antibacterial action and having the property of insolubility in solvents (especially water) while maintaining the antibacterial property of a positively charged organic compound, and discovered that the objects can be achieved by a polyelectrolyte complex obtained by reacting a specific anionic polymer and a specific cationic polymer. The present invention is based on the above discovery.

SUMMARY OF THE INVENTION

Therefore, the present invention relates to an antibacterial agent characterized by containing a polyelectrolyte complex obtained by reacting (A) a cationic polymer containing $N^+$ atoms in repeating units thereof and (B) an anionic polymer containing $—COO^-$ groups, $—SO_3^-$ groups, or $—PO_3^-$ groups in repeating units thereof.

Further, the present invention relates to an antibacterial material characterized by carrying the above-mentioned polyelectrolyte complex on a carrier.

According to a preferable embodiment of the present invention, as the cationic polymer (A), use is made of at least one compound selected from the group consisting of:

(a1) a compound (quaternary ammonium salt polymer) of the general formula (I):

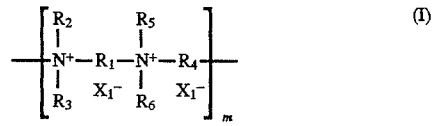

wherein $R_1$ and $R_4$ are, independently, an alkylene group of 1 to 10 carbon atoms, preferably a straight or branched alkylene group of 2 to 8 carbon atoms, a group of the general formula:

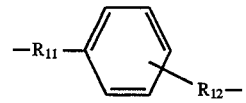

wherein $R_{11}$ and $R_{12}$ are, independently, an alkylene group of 1 or 2 carbon atoms, preferably $R_{11}$ and $R_{12}$ being bonded at the p-position, or an arylene group, and $R_2$, $R_3$, $R_5$, and $R_6$ are, independently, an alkyl group of 1 to 3 carbon atoms, or $R_1$ forms, together with the 2 nitrogen atoms and $R_2$, $R_3$, $R_5$, and $R_6$ in the above formula, a group of the formula:

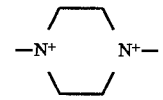

and $R_4$ has the same meaning as above, $X_1^-$ is a counter ion, and m is a number of 5 or more, (a2) a compound (quaternary ammonium salt polymer) of the general formula (II):

wherein A is a group of the general formula:

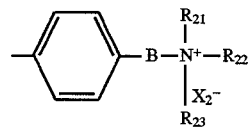

(wherein B is an alkylene group of 1 or 2 carbon atoms, $R_{21}$, $R_{22}$, and $R_{23}$ are, independently, a hydrogen atom or an alkyl group of 1 to 3 carbon atoms, and $X_2^-$ is a counter ion), or A is a group of the general formula:

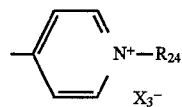

(wherein $R_{24}$ is an alkyl group of 1 to 3 carbon atoms or a benzyl group and $X_3^-$ is a counter ion), or A is a group of the general formula:

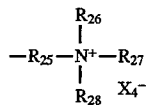

(wherein $R_{25}$ is an alkyl group of 1 or 2 carbon atoms, $R_{26}$, $R_{27}$, and $R_{28}$ are, independently, a hydrogen atom or an alkyl group of 1 to 3 carbon atoms, and $X_4^-$ is a counter ion) and n is a number of 10 or more, (a3) a compound (basic amino acid polymer) of the general formula (III):

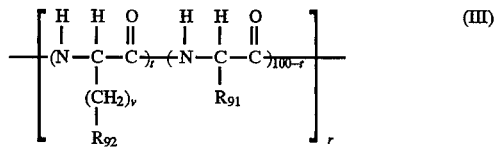

wherein v is 3 or 4, $R_{91}$ is a hydrogen atom; an alkyl group of 1 to 4 carbon atoms; an alkyl group of 1 to 4 carbon atoms substituted by a hydroxyl or mercapto group or by an alkylthio group of 1 to 3 carbon atoms; or an imidazolyl-methyl or indolylmethyl group; for example, a methyl, isopropyl, isobutyl, s-butyl, hydroxymethyl, hydroxyethyl, methylthioethyl, mercaptomethyl, 5-imidazolylmethyl or 3-imidazolylmethyl group, $R_{92}$ is $-N^+H_3X_5^-$ or $-N^+H_2C$ (NH) $NH_2X_6^-$, $X_5^-$ and $X_6^-$ are, independently counter ions, t is 20 to 100, and r is an integer of 10 or more, and (a4) a cationic polysaccharide.

Further, as the anionic polymer (B), use is made of at least one compound selected from the group consisting of:

(b1) a compound (acidic amino acid polymer) of the general formula (IV):

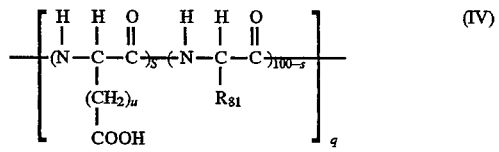

wherein u is 1 or 2, $R_{81}$ is a hydrogen atom, an alkyl group of 1 to 4 carbon atoms; an alkyl group of 1 to 4 carbon atoms substituted by a hydroxyl or mercapto group or by an alkylthio group of 1 to 3 carbon atoms; or an imidazolyl-methyl or indolylmethyl group; for example, a methyl, isopropyl, isobutyl, s-butyl, hydroxymethyl, hydroxyethyl, methylthioethyl, mercaptomethyl, 5-imidazolylmethyl or 3-imidazolylmethyl group, s is 20 to 100 and q is an integer of 10 or more, (b2) a compound (acrylic acid polymer) of the general formula (V):

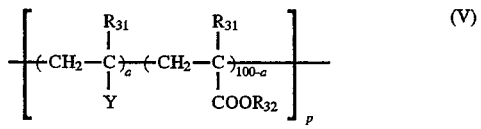

wherein $R_{31}$ is a hydrogen atom or a methyl group, $R_{32}$ is an alkyl group of 6 to 18 carbon atoms, preferably a straight or branched alkyl group of 6 to 14 carbon atoms, Y is a group of a carboxylic acid or a salt thereof, a sulfonic acid or a salt thereof or a phosphoric acid or a salt thereof, or an aryl group containing a group of a carboxylic acid or a salt thereof, a sulfonic acid or a salt thereof or a phosphoric acid or a salt thereof, a is a numeral of 20 to 100, preferably 50 to 100, and p is an integer of 10 or more, and (b3) an anionic polysaccharide.

BEST MODE FOR CARRYING OUT THE INVENTION

The polyelectrolyte complex (hereinafter optionally referred to as "PEC") per se which may be used in the present invention is a known substance. As described, for example, in Japanese Published Unexamined Patent Application No. 49-8581, a polyelectrolyte complex (PEC) can be immediately formed by mixing a solution of a cationic polymer (a polyelectrolyte having positive charges) and a solution of an anionic polymer (a polyelectrolyte having negative charges). The resulting PEC may be dissolveed in a particular three-component solvent (for example, water/acetone/low molecular weight salt with a particular composition), but is insoluble in a general solvent. A PEC film exhibits a high permeability for various low molecular weight compounds and so may be used as a dialysis membrane. PEC may be used to provide various types of materials having various properties according to the kind of the starting polymers (polyelectrolytes), the mixing ratio thereof, the preparation conditions, or the like. However, it was not known hitherto that PEC has an antibacterial property.

In the present specification, an alkyl group of 1 to 3 carbon atoms means, for example, a methyl, ethyl, or n- or i-propyl group. An alkyl group of 1 to 4 carbon atoms means, in addition to the above-mentioned alkyl group of 1 to 3 carbon atoms, for example, an n-, i-, s-, or t-butyl group. An alkylene group of 1 to 2 carbon atoms means, for example, a methylene, ethylene, or ethylidene group. A straight or branched alkylene group of 1 to 10 carbon atoms means, for example, a methylene, ethylene, propylene, trimethylene, tetramethylene, pentamethylene, hexamethylene, heptamethylene, octamethylene, nonamethylene, decamethylene, ethylethylene or ethyltrimethylene group. A straight or branched alkyl group of 6 to 18 carbon atoms means, for example, a straight alkyl group of 6 to 18 carbon atoms, an alkyl group of 6 to 15 carbon atoms substituted with one or more straight or branched alkyl groups of 1 to 3 carbon atoms, in particular, an alkyl group of 6 to 10 carbon atoms monosubstituted with a straight alkyl group of 1 to 3 carbon atoms. An arylene group means, for example, a phenylene or naphthalene group. A carboxylic acid salt group, a sulfonic acid salt group or a phosphoric acid salt group means, for example, a salt of an alkali metal (for example, sodium or potassium) or an alkaline earth metal (for example, calcium or magnesium). Further, an aryl group containing a sulfonic acid group or a salt thereof means, for example, a sulfophenyl group.

The counter ions present both in the starting cationic polymer (A) and starting anionic polymer (B) no longer exist in the PEC product prepared from the reaction therebetween. Therefore, the counter ions may be any ions so long as they do not interfere with the reaction therebetween. Preferable counter ions are halide ions, in particular chloride, bromide or iodide ions.

The PEC obtained by the reaction of the cationic polymer (A) and the anionic polymer (B) has a structure that the $N^+$ sites of the cationic polymer are successively bonded to the acid sizes (for example, carboxylic, sulfonic, or phosphoric acid sites) of the anionic polymer by means of Coulomb energy. Namely, the starting polymers are cross-linked to each other by ionic bonds and form a gel which is insoluble in a solvent.

For example, the PEC produced from the cationic polymer (a1) of the general formula (i) and the anionic polymer (b1) of the general formula (IV) has the structure of the general formula (VI):

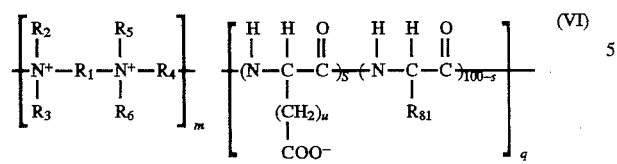

wherein $R_1$, $R_2$, $R_3$, $R_4$, $R_5$, $R_6$, $R_{81}$, m, u, s, and q have the same meanings as mentioned above, except that $0.25 \leq 2m/q \leq 4.0$.

Further, the PEC produced from the cationic polymer (a1) of the general formula (I) and the anionic polymer (b2) of the general formula (V) has the structure of the general formula (VII):

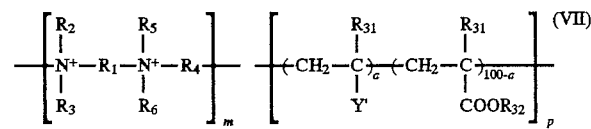

wherein $R_1$, $R_2$, $R_3$, $R_4$, $R_5$, $R_6$, $R_{31}$, $R_{32}$, m, a, and p have the same meanings as mentioned above, except that $0.25 \leq 2m/p \leq 4.0$, and Y' is a —COO$^-$, —SO$_3^-$ or PO$_2^-$ or PO$_3$H$^-$ group, or Y' is an aryl group containing a —COO$^-$, —SO$_3^-$ or PO$_2^-$ or PO$_3$H$^-$ group.

Further, the PEC produced from the cationic polymer (a2) of the general formula (II) and the anionic polymer (b1) of the general formula (IV) has the structure of the general formula (VIII) or (IX):

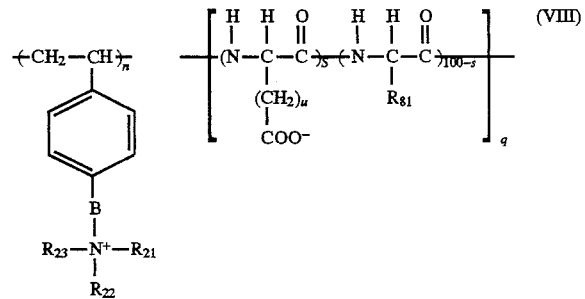

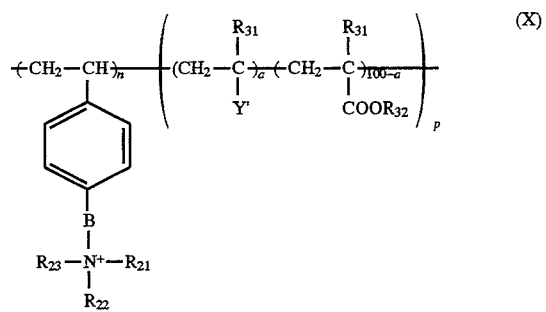

In the above formulae (VIII) and (IX), B, $R_{21}$, $R_{22}$, $R_{23}$, $R_{24}$, $R_{81}$, n, u, s, and q have the same meanings as mentioned above, except that $0.25 \leq n/q \leq 4.0$.

The PEC produced from the cationic polymer (a2) of the general formula (II) and the anionic polymer (b2) of the general formula (V) has the structure of the general formula (X) or (XI):

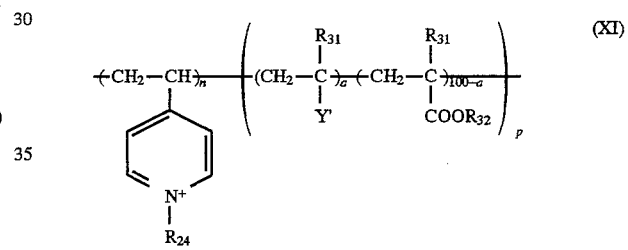

In the above formulae (X) and (XI), B, $R_{21}$, $R_{22}$, $R_{23}$, $R_{24}$, $R_{31}$, $R_{32}$, Y', n, a, and p have the same meanings as mentioned above, except that $0.25 \leq n/p \leq 4.0$.

The PEC produced from the cationic polymer (a3) of the general formula (III) and the anionic polymer (b1) of the general formula (IV) has the structure of the general formula (XII):

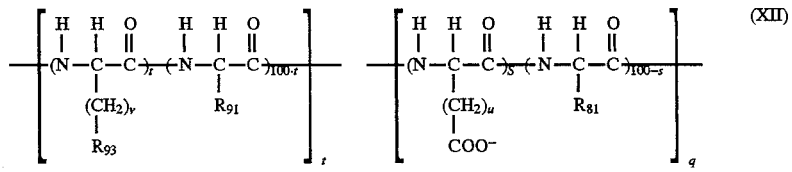

wherein $R_{91}$, $R_{81}$, r, t, v, q, u, and s have the same meanings as mentioned above, except that $0.25 \leq r/q < 4.0$, and $R_{93}$ is a N$^+$H$_3$X$_5^-$ or —N$^+$H$_2$C(NH)NH$_2$X$_6^-$ group.

The PEC produced from the cationic polymer (a3) of the general formula (III) and the anionic polymer (b2) of the general formula (V) has the structure of the general formula (XIII):

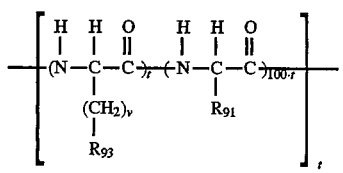 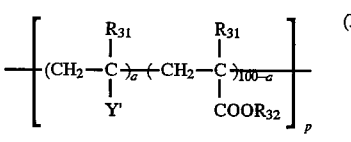 (XIII)

wherein $R_{91}$, $R_{93}$, $R_{31}$, $R_{32}$, Y', r, t, v, a, and p have the same meanings as mentioned above, except that $0.25 \leq r/p \leq 4.0$.

The PEC which can be used as an antibacterial agent in the present invention is not limited so long as being a solid insoluble in a solvent. The average molecular weight thereof is not particularly limited, but the number of ion sites in the PEC is generally 10 to 1000, preferably 20 to 100. The average molecular weights of the starting anionic polymer (a1) to (a4) and the starting cationic polymer (b1) to (b3) are not particularly limited, but as to the preferable range thereof, m in the general formula (I) [the cationic polymer (a1)] is 5 to 500 (in particular 5 to 100), n in the general formula (II) [the cationic polymer (a2)] is 10 to 1000 (in particular 10 to 500), and r in the general formula (III) [the cationic polymer (a3)] is 10 to 1000 (in particular 10 to 500). Further, q in the general formula (IV) [the anionic polymer (b1)] is 10 to 1000 (in particular 10 to 500), and p in the general formula (V) [the anionic polymer (b2)] is 10 to 1000 (in particular 10 to 500).

As examples of the cationic polymer (a1) of the general formula (I), there may be mentioned quaternary polyethyleneimine chloride, poly(N,N,N',N'-tetramethyl-alkylene-p-xylylene diammonium dichloride), poly(N,N,N',N'-tetramethyl-alkylene-diammonium dichloride), poly(N,N-dimethyl-3-hydroxypropylammonium chloride), poly(2-hydroxy-3-methacroyloxypropyltrimethylammonium chloride), poly(2-methacroyloxyethyltrimethylammonium chloride), poly(glycidyltrimethyl-ammonium chloride), poly[(dimethyliminio) ethylene (dimethyliminio)-methylene-1,4-phenylenemethylene dichloride] [in general known as 2X], poly[(dimethyliminio)hexamethylene (dimethyliminio)methylene-1,4-phenylenemethylene dichloride] [in general known as 6X], poly[(dimethyliminio) hexamethylene chloride] [in general known as 6,6], poly(N-ethyl-4-vinylpyridinium bromide), or the like.

As examples of the cationic polymer (a2) of the general formula (II), there may be mentioned poly (vinylbenzyltrimethylammonium chloride), polyvinylpyridinium chloride, poly(N -benzyl-4-vinylpyridinium chloride), or the like.

As examples of the cationic polymer (a3) of the general formula (III), there may be mentioned polylysine, polyarginine or copolymers thereof, or copolymers of the monomers of said polymers with glycine, alanine, phenyl alanine, tyrosine, valine, leucine, isoleucine, serine, threonine, methionine, cysteine, histidine, proline, and/or tryptophan, or the like.

Examples of the cationic polysaccharide (a4) are as follows:

(1) Chitosan and derivatives thereof:

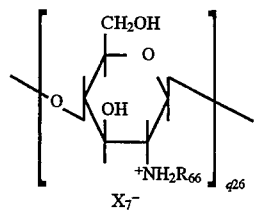

wherein $R_{66}$ is a hydrogen atom or an acetyl group, $X_7^-$ is a counter ion, the deacetylization degree is 50 to 100 percent, preferably 70 to 100 percent, $q_{26}$ is 20 to 3000, preferably 50 to 1000. It is noted that in the above formula, the $N^+$ atoms in the $-N^+H_2R_{66}$ groups and the anionic groups in the anionic polymer are bonded to each other.

(2) Diethylaminoethyl Derivative of Neutral Polysaccharide:

As a neutral polysaccharide, there may be mentioned dextran, cellulose, mannan, starch, agarose or the like. The degree of diethylaminoethyl substitution of the above derivatives is 0.5 to 2.0, preferably 0.7 to 1.5 groups per one sugar residue. The degree of polymerization is 50 to 5000, preferably 100 to 1000. It is noted that the nitrogen atoms in the diethylaminoethyl groups and the anionic groups in the anionic polymer are bonded to each other.

Examples of the anionic polymer (b1) of the general formula (IV) are polyglutamic acid, polyaspartic acid, or copolymers thereof, and copolymers of the monomers of said polymers with glycine, alanine, phenylalanine, tyrosine, valine, leucine, isoleucine, serine, threonine, methionine, cysteine, histidine, proline, and/or tryptophan, or the like.

It is noted that the polyamino acids of the general formulae (III) and (IV) may be prepared by the general acid anhydride monomer method, the active esterification method, the Merryfield method, or the like.

As examples of the anionic polymer (b2) of the general formula (V), there may be mentioned polyacrylic acid, polymethacrylic acid, polyitaconic acid monoesters, polymaleic acid monoesters, polyvinylsulfonic acid, polystyrene sulfonic acid, and copolymers of two or more monomers constituting the above polymers, and copolymers of such monomers with carboxylic acid derivatives having $C_6$ to $C_{18}$ alkyl groups bonded by esterification to the carboxylic groups of the above monomers.

Examples of the anionic polysaccharide (b3) are as follows:

(1) Hyaluronic Acid and Derivatives Thereof

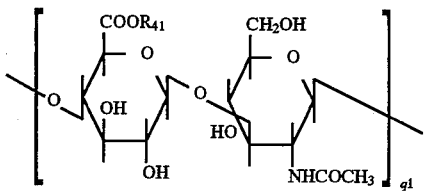

wherein $R_{41}$ is a hydrogen atom or an alkaline metal (for example, sodium or potassium), but disappears in at least a portion of the repeating units in the PEC prepared by the reaction with a cationic polymer, and $q_1$ is 100 to 12000, preferably 200 to 8000.

(2) Alginic Acid and Derivatives Thereof

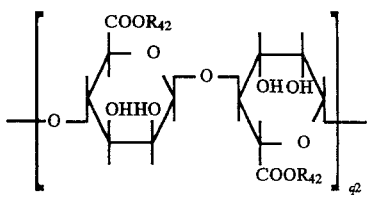

wherein $R_{42}$ is a hydrogen atom or an alkaline metal (for example, sodium or potassium), but disappears in at least a portion of the repeating units in the PEC prepared by the reaction with the cationic polymer, and $q_2$ is 100 to 10000, preferably 200 to 5000.

(3) Chondroitin Sulfuric Acid A

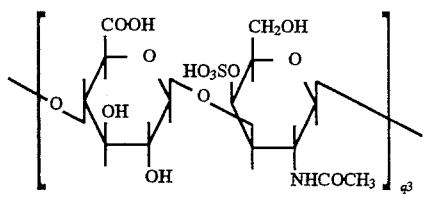

wherein $q_3$ is 10 to 100, preferably 10 to 50, and at least a portion of the COOH and/or $SO_3H$ groups in the formula is converted to $COO^-$ and/or $SO_3^-$ groups by reaction with the cationic polymer.

(4) Chondroitin Sulfuric Acid C

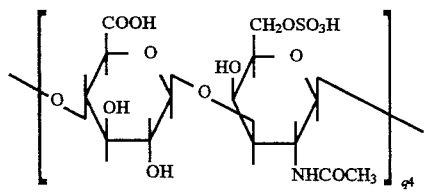

wherein $q_4$ is 10 to 100, preferably 10 to 50, and at least a portion of the COOH and/or $SO_3H$ groups in the formula is converted to $COO^-$ and/or $SO_3^-$ groups by reaction with the cationic polymer.

(5) Chondroitin Sulfuric Acid B (Dermatan Sulfuric Acid) and Derivatives Thereof

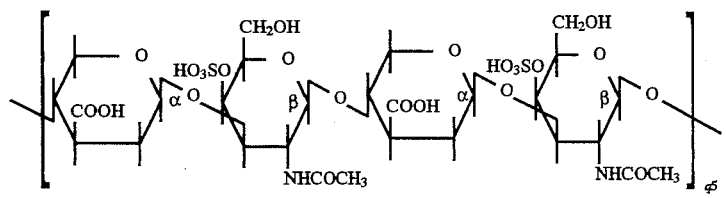

wherein $q_5$ is 20 to 100, preferably 40 to 50, and at least a portion of the COOH and/or $SO_3H$ groups in the formula is converted to $COO^-$ and/or $SO_3^-$ groups by reaction with the cationic polymer.

(6) Chondroitin Sulfuric Acid D and Derivatives Thereof

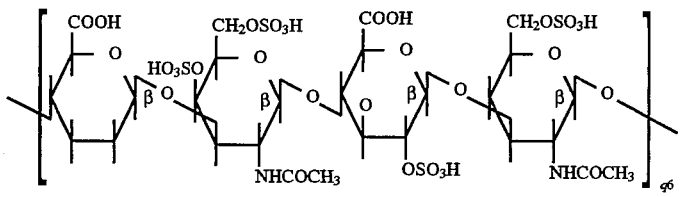

wherein $q_6$ is 10 to 500, preferably 20 to 100, and at least a portion of the COOH and/or SO$_3$H groups in the formula is converted to COO$^-$ and/or SO$_3^-$ groups by reaction with the cationic polymer.

(7) Chondroitin Sulfuric Acid E and Derivatives Thereof

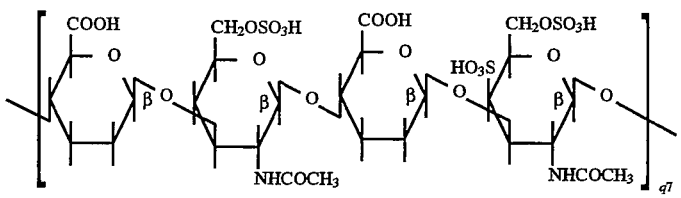

wherein $q_7$ is 10 to 300, preferably 20 to 100, and at least a portion of the COOH and/or SO$_3$H groups in the formula is converted to COO$^-$ and/or SO$_3^-$ groups by reaction with the cationic polymer.

(8) Heparan Sulfuric Acid and Derivatives Thereof

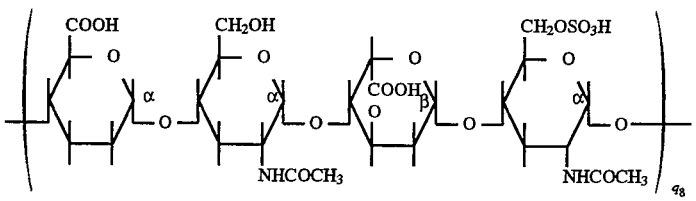

wherein $q_8$ is 7 to 200, preferably 10 to 100, and at least a portion of the COOH and/or SO$_3$H groups in the formula is converted to COO$^-$ and/or SO$_3^-$ groups by reaction with the cationic polymer.

(9) Heparin and Derivatives Thereof

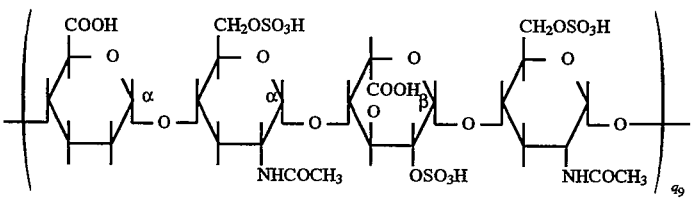

wherein $q_9$ is 100 to 500, preferably 100 to 300, and at least a portion of the COOH and/or SO$_3$H groups in the formula is converted to COO$^-$ and/or SO$_3^-$ groups by reaction with the cationic polymer.

(10) κ-Carragheenan and Derivatives Thereof

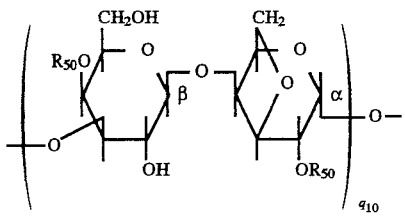

wherein $R_{50}$ is a hydrogen atom or $SO_3H$ group, $q_{10}$ is 100 to 10000, preferably 100 to 500, and at least a portion of the $SO_3H$ groups in the formula is converted to $SO_3^-$ groups by the reaction with the cationic polymer.

(11) λ-Carragheenan and Derivatives Thereof

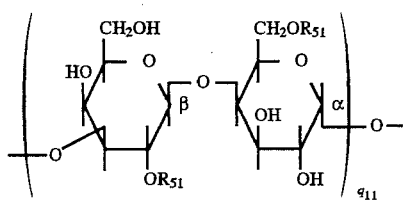

wherein $R_{51}$ is a hydrogen atom or $SO_3H$ group, $q_{11}$ is 100 to 10000, preferably 100 to 500, and at least a portion of the $SO_3H$ groups in the formula is converted to $SO_3^-$ groups by the reaction with the cationic polymer.

Further, after carboxymethylation, sulfation, phosphoriration or the like, neutral natural polysaccharide may be converted to and used as the anionic polysaccharide (b3). Examples of such modified polysaccharides are as follows:

(12) Cellulose Derivatives

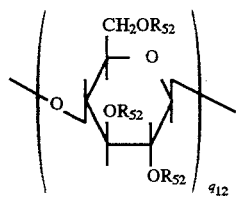

wherein $R_{52}$ is a hydrogen atom, or a carboxymethyl, sulfuric acid or phosphoric acid group, $q_{12}$ is 100 to 15000, preferably 200 to 5000, and at least a portion of the COOH, $SO_3H$ and/or $PO_3H_2$ groups in the formula is converted to $COO^-$, $SO_3^-$ and/or $PO_3^{2-}$ or $PO_3H^-$ groups by the reaction with the cationic polymer.

(13) Chitin Derivatives

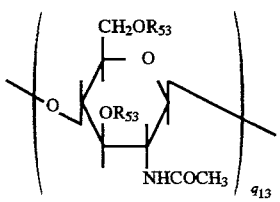

wherein $R_{53}$ is a hydrogen atom, or a carboxymethyl, sulfuric acid or phosphoric acid group, $q_{13}$ is 50 to 8000, preferably 100 to 5000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(14) Carboxymethylstarch and Derivatives Thereof

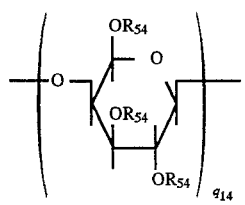

wherein $R_{54}$ is a hydrogen atom, or a carboxymethyl, sulfuric acid or phosphoric acid group, $q_{14}$ is 100 to 8000, preferably 200 to 5000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(15) Amylose Derivatives

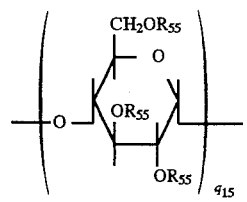

wherein $R_{55}$ is a hydrogen atom, or a carboxymethyl, sulfuric acid or phosphoric acid group, $q_{15}$ is 100 to 8000, preferably 100 to 5000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(16) Amylopectin Derivatives

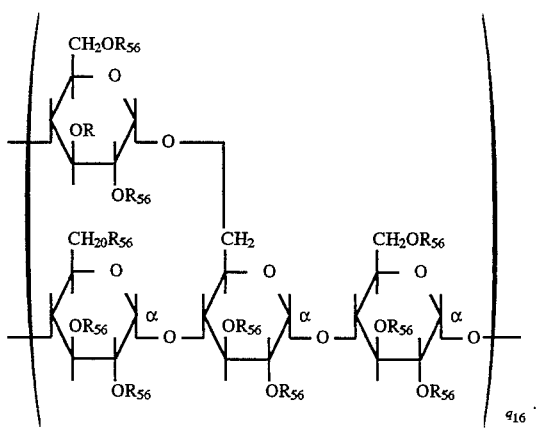

wherein $R_{56}$ is a hydrogen atom, or a carboxymethyl, sulfuric acid or phosphoric acid group, $q_{16}$ is 100 to 100000, preferably 100 to 10000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(17) β-1,3'-Glucan Derivatives (For Example, Cardran)

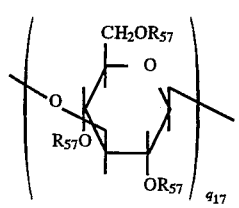

wherein $R_{57}$ is a hydrogen atom, or a carboxymethyl, sulfuric acid or phosphoric acid group, $q_{17}$ is 50 to 1000, preferably 100 to 300, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(18) β-1,2'-Glucan Derivatives

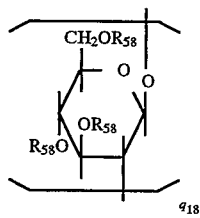

wherein $R_{58}$ is a hydrogen atom, or 8 carboxymethyl, sulfuric acid or phosphoric acid group, $q_{18}$ is 100 to 4000, preferably 100 to 3500, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(19) β-1,3'-; β-1,6'-Glucan (For Example Lentinan, Schizophilan, Coriolan) Derivatives

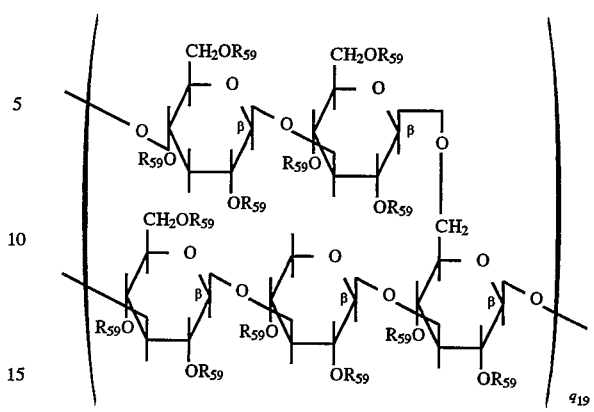

wherein $R_{59}$ is a hydrogen atom, or a carboxymethyl, sulfuric acid or phosphoric acid group, $q_{19}$ is 100 to 100000, preferably 100 to 50000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(20) Dextran Derivatives

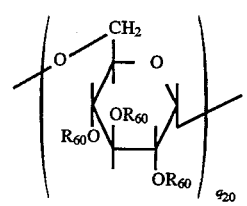

wherein, $R_{60}$ is a hydrogen atom, or a carboxymethyl, sulfuric acid or phosphoric acid group, $q_{20}$ is 100 to 300000, preferably 200 to 100000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(2) Pullulan Derivatives

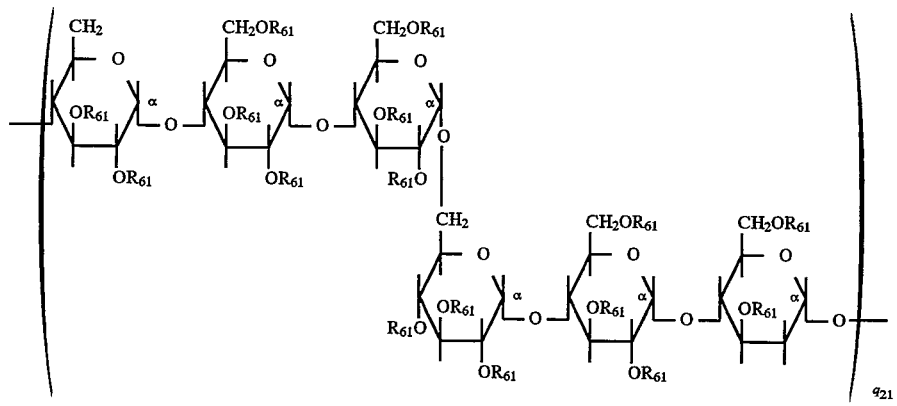

wherein $R_{61}$ is a hydrogen atom, or a carboxymethyl, sulfuric acid or phosphoric acid group, $q_{21}$ is 300 to 2000, preferably 500 to 1500, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(22) Agarose Derivatives

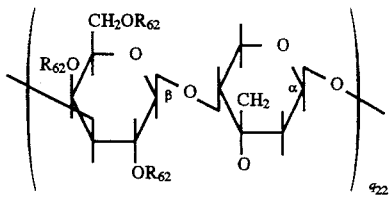

wherein $R_{62}$ is a hydrogen atom, or a carboxymethyl, sulfuric acid or phosphoric acid group, $q_{22}$ is 20 to 200, preferably 20 to 100, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(23) β-1,4'-Galactan Derivatives

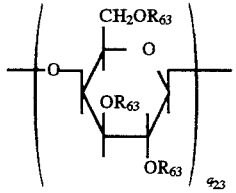

wherein $R_{63}$ is a hydrogen atom, or a carboxymethyl, sulfuric acid or phosphoric acid group, $q_{23}$ is 50 to 200, preferably 50 to 100, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(24) Mannan Derivatives

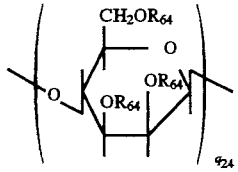

wherein $R_{64}$ is a hydrogen atom, or a carboxymethyl, sulfuric acid or phosphoric acid group, $q_{24}$ is 50 to 5000, preferably 100 to 3000, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

(25) Inulin Derivatives

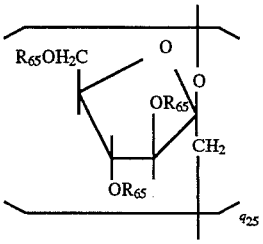

wherein $R_{65}$ is a hydrogen atom, or a carboxymethyl, sulfuric acid or phosphoric acid group, $q_{25}$ is 20 to 100, preferably 20 to 80, and at least a portion of the COOH, $SO_3H$ and/or $PO_3H_2$ groups in the formula is converted to $COO^-$, $SO_3^-$ and/or $PO_3^{2-}$ or $PO_3^{H-}$ groups by the reaction with the cationic polymer.

The polyelectrolyte complex (PEC) used in the present invention may be prepared by a usual method. More particularly, the reaction of aqueous solutions of the above-mentioned cationic polymers and anionic polymers ($10^{-5}$ mole/liter to $10^{-2}$ mole/liter) is carried out in aqueous solution within 0.25 to 4.0, preferably 0.4 to 2.5, of a concentration ratio of the cationic sites of the cationic polymer and the anionic sites of the anionic polymer (cationic sites/anionic sites). If the concentration ratio of the cationic sites and anionic sites (cationic sites/anionic sites) goes out of the above range of 0.25 to 4.0, it becomes difficult to form the polyelectrolyte complex (PEC). The above reaction has a relatively high reactivity. Therefore, the pH of the solution, the ionic strength, the temperature or the like may vary in a relatively wide range, but in general the reaction is carried out at a pH of 3 to 9, an ionic strength of 0 to 1.0, and a temperature of 20° to 40° C.

The charge balance of the PEC used in the present invention is −6 to +6, preferably −4.5 to +4.5. In the present specification, the term "charge balance" means the charge state of the PEC, expressed by the concentration ratio of the cationic sites of the starting cationic polymer and the anionic sites of the starting anionic polymer. For example, when the concentrations of the cationic sites of the cationic polymer used and the anionic sites of the anionic polymer used are equal to each other, the charge balance of the PEC produced becomes ±0. If the concentration ratio is greater than that of the above case (namely, the concentration of the cationic sites is higher), the charge balance becomes positive, while if the concentration ratio is smaller (namely, the concentration of the anionic sites is higher), the charge balance becomes negative. Further, when the concentration ratio is 1.5, the charge balance becomes +2, while when the concentration ratio is 0.5, the charge balance becomes −3.3. The charge balance may be easily adjusted by changing the amount used of the aqueous solution of the cationic polymer and the aqueous solution of the anionic polymer, each having the equal concentration, respectively. By adjusting the charge balance, it is possible to obtain an excess cationic or anionic state.

The polyelectrolyte complex (PEC) is obtained as a gelanious precipitate from the reaction solution. Therefore, the PEC may be used in the form of the resulting gelanious precipitate, or directly shaped and processed to a suitable form (for example, a fiber, film, sheet, block, latex, or gel) and used as an antibacterial material in a wet or dry state. Further, the PEC can be deposited or adhered on almost all materials, and thus can be coated on a suitable carrier to prepare an antibacterial material. If an antibacterial property is imparted to a liquid per se depending on the application thereof, the PEC reaction solution may also be directly used in the form of suspended liquid.

As the carrier made of an organic material, there may be mentioned, for example, an organic polymer material, such as, synthetic or natural resin, synthetic or natural rubber, synthetic or natural fibers, biopolymer materials, leather, wood, pulp, and paper.

As the synthetic resin, there may be mentioned, for example, hydrocarbon polymers (for example, polyolefin, polyethylene, polypropylene, polybutene-1, poly-4-methylpentene-1, polystyrene, polyacetylene); halogenated hydrocarbon polymers (for example, polyvinyl chloride, polyvinylidene chloride, fluorine resin); unsaturated alcohol or ether polymers (for example, polyvinyl alcohol, polyvinyl ether, polyphenylene oxide, polyphenylene sulfide, polyacetal, polyether, polyvinylbutyral, polyether sulfonepoxy resin); unsaturated aldehyde or ketone polymers (for example, phenol and urea resin); unsaturated carboxylic acid polymers (for example, acrylic resin); unsaturated ester polymers (for example, polyvinyl ester, polyacrylate, wholly aromatic polyester, polyethylene terephthalate, polycarbonate, polybutylenediallylphthlate, unsaturated polyester resin); unsaturated nitrile polymers (for example, polyacrylonitrile, ABS resin, AAS resin, AES resin); unsaturated amine polymers (for example, polyvinylamine, polyimide, polyamide, melamine resin, polyethyleneimine, polyurethane); and also silicone resins, the copolymers or blended resins of above-mentioned polymers, and thermoplastic elastomers. Example of the natural resins is cellulose derivative resins.

As the synthetic rubber, there may be mentioned, for example, styrene-butadiene, butadiene, isoprene, nitro, chloroprene, butyl, ethylene-propylene, acrylic, chlorinated polyethylene, fluoro, silicone, urethane and polysulfide rubber.

As the synthetic fiber, there may be mentioned, for example, regenerated cellulose acetate (viscose rayon, cuprammonium rayon), triacetate, polyamide, acryl, vinylon, vinylidene, polyvinyl chloride, polyester, polyethylene, polypropylene, polybenzoate, polycral, aramide phenolic fiber, polyurethane fiber, fluorine fiber, polyvinyl alcohol, carbon fiber, and silicon carbide fiber. Examples of the natural fiber are cotton, silk, wool, hemp, and wood.

As the carrier, there may also be used inorganic materials, for example, glass, minerals (for example, asbestos), enamel, cement, ceramics, artificial stone, and metals (for example, iron, steel, non-ferrous metals, alloys). The shape and form of the carrier are not particularly limited and may be any of a fiber, filament, film, sheet, woven fabric, nonwoven fabric, bar, string, sphere, powder, granule, porous body, hollow body, aggregate, foam, gel, and the like.

The PEC can be carried on the carrier by any known method, for example, coating, spraying, dipping, or the like. It is sufficient to merely bring the PEC solution into contact with the carrier. For example, the PEC can be strongly adhered on the bottom of a container by mixing the aqueous solution of the cationic polymer and the aqueous solution of the anionic polymer in a reaction vessel, then transferring the reaction solution immediately to said container, allowing to stand overnight or so to sufficient precipitate the PEC, then removing the supernatant from the container, washing with physiological saline solution and distilled water about one to three times, and drying at 60° to 100° C. for 6 to 12 hours for annealing. The entire inside surface of a container can be strongly coated with the PEC, by agitating the solution while rotating overnight or so to sufficiently precipitate the PEC, then removing the supernatant from the container, washing and annealing in the same manner as above.

Further, in the case of a fiber, bead, woven fabric or the like, such materials map be treated in the same manner as mentioned above, after dipping in the PEC solution overnight or so. Further, as described in Japanese Published Unexamined Patent Application No. 50-63096, it is possible to prepare the PEC in the presence of a water-soluble organic solvent (for example, a mixture of water, acetone, and sodium bromide), and directly use the reaction solution as a coating agent for coating, spraying or dipping.

When the PEC is carried on a highly hydrophobic surface of the carrier (for example, a polycarbonate carrier), it is preferable to perform the treatment for imparting hydrophilic property to the surface (for example, treatment with hypochloric acid, organic solvent, plasma, or ultraviolet radiation) in advance.

The resulting carrier carrying the PEC thereon may be directly used as an antibacterial material without further processing. Further, such an antibacterial material may be used to prepare various antibacterial products. As examples of the antibacterial materials which can be used without further processing, there may be mentioned a textile material (for example, fiber, filament, woven fabric, or nonwoven fabric) carrying the PEC on at least a part of the surface thereof (preferably, the entire surface thereof), for example, PEC carrying gauze, absorbent cotton, or fabric (for sterile clothing products for medical, sanitation, or beauty use). From the above PEC carrying fiber materials, it is possible to simply prepare, for example, masks, eye bandages, bandages, sheets, absorbent pads (for example, for the ears, nose or mouth, or menstrual tampons), and napkins.

Further, it is possible to prepare various types of sterile clothing, for example, underwear (undershirts, undergarments, socks, etc.), baby linen products (for example, baby underpants, bibs, swaddling clothes, singlets, etc.), handkerchiefs, corsets, girdles, brassieres, swimming suits, surgical operation garments, surgical and patient use aprons, life-saying devices, diving suits, laboratory clothing, protective clothing (surgical gloves), masks, and surgical hats.

The antibacterial products prepared using the PEC carrying antibacterial materials are not particularly limited, so long as the suppression of the proliferation of microorganisms is desired therein. For example, there may be mentioned medical devices, sanitation devices (for example, hospital-use bed covers, sheets, sterile clothing, bandages, diapers, eye bandage Gauze, tampons, contact lenses, contact lens containers, pharmaceutical storing containers, blood transfusion containers), food devices (for example, food packaging materials and food storage containers), household devices (for example, devices for dining table use, kitchenware such as a bottom sheet for a cupboard, sanitaryware such as toiletseat covers), barber and beauty shop devices, devices where slime easily occurs (for example, dialysis membranes and filter materials), and physicochemical machinery and equipment (for example, humidifiers, washers, and constant temperature tanks), etc.

Particularly preferable examples of the medical devices (more preferably disposable medical devices) as the antibacterial products prepared from the PEC carrying antibacterial material of the present invention will be mentioned hereinafter. The preferred carrier materials therefor are shown in parentheses.

As general medical and nursing devices, there may be mentioned, for example, adapters [or connectors] (polyethylene, polypropylene, or polyamide), irrigators (polyvinyl chloride), indicators (Japanese and western style paper), aprons (nonwoven fabrics), diapers (polypropylene fibers, nonwoven fabrics, paper, cotton, polyamide, pulp), gauze (nonwoven fabrics, paper, paper cotton, polyamide, acrylics, polyester), cups [specimen containers] (polypropylene, polyethylene, polystyrene, paper), catheters [tubes] (polyvinyl chloride, rubber, silicone, polyethylene, polypropylene, polyamide), covers (nonwoven fabrics, polyethylene), cuffs (polyvinyl chloride, rubber), eye bandages (gauze, nonwoven fabrics, synthetic fibers), enema devices (synthetic fibers), caps (nonwoven fabrics, paper), suction devices (polyvinyl chloride, plastics, rubber), clamps [clips] (sponge, rubber, metals, polyamide, polyvinyl chloride, acetal resins), examination clothing (nonwoven fabrics), coils [for heating blood] (polyvinyl chloride, polypropylene), oxygen tents (polyethylene, polyvinyl chloride), three-way plugs (polyamide, polyacetal, Derlin, polyvinyl chloride, polymethyl pentene), artificial noses (paper, polypropylene), stoppers (polyethylene, polystyrene, polypropylene), blood transfusion sets (polyethylene, polystyrene, polypropylene, rubber, polyvinyl chloride, metals), towels (nonwoven fabrics), cavity scopes (polyvinyl chloride), syringes (rubber, polypropylene, medical use silicone oil, polymethylpentene), needles (polyethylene, stainless steel, polypropylene, polyvinyl chloride), hearing aids (polyvinyl chloride), proctoscopes (polyvinyl chloride), tapes [sticking plasters] (acrylics, polyester, polyethylene, cotton, Japanese paper, polyvinyl chloride, polyamide, rayon), T-bandages (nonwoven fabrics, paper), gloves (polyethylene, polyvinyl chloride, rubber), instillators (polyethylene, polypropylene), trays (compressed pulp, paper), urinals (polyester, polyethylene, polypropylene, polyvinyl chloride, ABS, rubber), name bands (polyvinyl chloride, polyethylene), pus basins (paper, pulp), bags (polyvinyl chloride, stainless steel, polyethylene, polystyrene, rubber, paper), pads [cotton] (cotton, gauze, polyester beads, nonwoven fabrics, paper), acupuncture needles (stainless steel), splints (polyisoprene), belts (spandex), cast bandages (cotton, gauze, knitted fabrics, nonwoven fabrics, plaster, polyamide), mouthpieces (polystyrene, paper), masks (polypropylene, polyethylene, polyamide, polyvinyl chloride, nonwoven fabrics), mats (polyethylene, aluminum, adhesives), manometers (polystyrene), cotton balls (cotton), cotton swabs (white birch material), finger sacks (polyethylene, rubber), indwelling needles (stainless steel, polyvinyl chloride, ABS, rubber, metals, polyethylene, polypropylene, fluororesins), connecting tubes (polyvinyl chloride, polyethylene, rubber, metals, polypropylene, polyamide), and the like.

Further, as anesthetic and surgical devices, there may be mentioned, for example, intrafusers for use of vascular injection (polyvinyl chloride, ABS, polyethylene, polypropylene, rubber, metals, Teflon), airways (polyvinyl chloride, ethylene/vinyl acetate copolymer), blepharostats (tantalum), gowns (nonwoven fabrics), catheters (polyvinyl chloride, polyvinyl chloride with mixed silicone, latex, stainless steel, Teflon), shoe covers (nonwoven fabrics), cuffs (latex), caps (nonwoven fabrics, cellulose), suction devices [suction tubes] (polyvinyl chloride, polyamide, polypropylene), pharyngoscopes (polyvinyl chloride), connectors (polyethylene), vascular injection sets (polyethylene, polypropylene, polyacetal, Teflon, polyvinyl chloride, metals, silicone), towels (nonwoven fabrics), counter electrode plates (aluminum foil, copper, stainless steel foil, Bose paper, stainless steel plate), tapes (nonwoven fabrics, filaments), gloves (rubber, polyethylene), drapes (polyvinyl chloride, polyethylene film, nonwoven fabrics), drains (polyvinyl chloride, rubber, silicone rubber), biopsy needles (stainless steel, ABS, polyvinyl chloride, polystyrene, metals), suture thread (silk, polyamide, polypropylene, polyester, stainless steel, catgut), masks (polyester, nonwoven fabrics, glass fibers, polystyrene), scalpels (stainless steel, polyvinyl chloride, ABS), and the like.

Furthermore, as examination and examination room devices, there may be mentioned, for example, cover glass (glass), blood sample tubes (glass, acrylics, polypropylene, natural rubber, synthetic rubber), blood sample bottles (polypropylene, polyethylene, polystyrene), test tubes (polypropylene, polyethylene, styrene resins, glass), petri dishes (polystyrene, paper, glass), Spitz tubes (polypropylene, polystyrene, acetyl cellulose, acrylics), plungers (polyethylene), slide glass (glass), tapes (paper), electrodes [for electrocardiograph etc.] (synthetic fiber, paper, lead wire, polyethylene, gel), incubators (polyethylene, glass, acrylics, synthetic rubber, polystyrene), beakers (polypropylene), pipettes (glass, polypropylene), labels (paper), and the like.

Further, as artificial organs and artificial kidney room devices, there may be mentioned, for example, catheters [cannulas] (Teflon, silicone rubber, polyvinyl chloride, polyethylene, polypropylene, cotton), blood circuits (rubber, polyvinyl chloride, polypropylene, polyamide, cellulose), connectors (polyamide, polyvinyl chloride, rubber, silicone, Teflon), artificial veins (silicone, Dacron, Teflon), artificial lungs (polycarbonate, polypropylene, polyamide, urethane foam, polyvinyl chloride), dialyzers (Cuprophane, polypropylene, polystyrene, silicone rubber, polyvinyl chloride, nonwoven fabrics, Japanese paper), dialysis membranes (Cuprophane, polyacrylonitrile), heat exchangers (silicone rubber, stainless steel), needles (polyethylene, stainless steel, polyvinyl chloride, polyamide, rubber, Teflon), filters (polycarbonate, Dacron wool, polypropylene), and the like. Further, the antibacterial products according to the present invention may be applied to various facilities (walls, floors, equipment, air filters, etc.) for maintaining a sterile atmosphere, endoscopes, and other things coming into direct contact with the human body.

In a cationic polyelectrolyte such as a cationic polymer, the counter ions carried thereon are generally low molecular weight counter ones (for example, halogen ions), and so is relatively easily separated from the polymer and thus the cationic sites in the polymer is easily exposed. To the contrary, in the PEC used in the present invention, the counter ions are polymeric compounds, and so the properties of quaternary ammonium from the starting cationic polymer are somewhat neutralized. It should be surprised that the PEC with such a structure exhibits antibacterial activity. The reason is not elucidated at present, but it is assumed that the quaternary ammonium portions strongly chemically bonded and contained in the polymer per se exhibit a sustained antibacterial activity. Further, a PEC generally exhibits remarkably diverse properties along with changes in the microdomain structure having the hydrophilic property, the structural changes in the surface water, changes in the charge balance or the like, and thus, it is assumed that these effects also serve the manifestation of the antibacterial property in the PEC of the present invention.

EXAMPLES

The present invention now will be further illustrated by, but by no means limited to, the following examples. It is noted that the average molecular weights described in the following examples are number average molecular weights measured by the vapor pressure osmometer method.

Preparation Example 1: Preparation of PEC (2X-CLA)

A cationic polymer, poly[(dimethyliminio) ethylene-(dimethyliminio)-methylene-1,4-phenylenemethylene dichloride] (2X) (average molecular weight=about 6000), in an amount of 0.015 g ($1\times10^{-4}$ moles as cationic sites), and an anionic polymer, acrylic acid/lauryl acrylate random copolymer (CLA) (acrylic acid content=about 80 mole percent; average molecular weight=about 10,000), in an amount of 0.018 g ($1\times10^{-4}$ moles as anionic sites) were dissolved separately in 10 ml of physiological saline solution (pH 7.4). The two aqueous solutions (5 ml, respectively) were mixed in a beaker to form a polyelectrolyte complex gel (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Further, 3 ml of the aqueous solution of the cationic polymer and 7 ml of the aqueous solution of the anionic polymer prepared in the same manner as above were mixed together in a beaker to form a polyelectrolyte complex gel (charge balance=−4).

Preparation Example 2: Preparation of PEC (2X-COA)

A cationic polymer, poly[(dimethyliminio)ethylene-(dimethyliminio)-methylene-1,4-phenylenemethylene dichloride] (2X) (average molecular weight=about 3000), in an amount of 0.015 g ($1\times10^{-4}$ moles as cationic sites), and an anionic polymer, acrylic acid/2-ethylhexyl acrylate random copolymer (COA) (acrylic acid content=about 60 molar percent; average molecular weight=about 8000), in an amount of 0.021 g ($1\times10^{-4}$ moles as anionic sites) were separately dissolved in 10 ml of distilled water (pH 8.0). The two aqueous solutions (5 ml, respectively) obtained were mixed together in a beaker to form a polyelectrolyte complex gel (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Further, 3 ml of the aqueous solution of the cationic polymer and 7 ml of the aqueous solution of the anionic polymer prepared in the same manner as above were mixed together in a beaker to form a polyelectrolyte complex gel (charge balance=−4).

Preparation Example 3: Preparation of PEC (PVBMA-COA)

A cationic polymer, poly (vinylbenzyltrimethylammonium chloride) (PVBMA) (average molecular weight=about 15000), in an amount of 0.021 g ($1\times10^{-4}$ moles as cationic sites), and an anionic polymer, acrylic acid/2-ethylhexyl acrylate random copolymer (COA) (acrylic acid content=about 60 mole percent; average molecular weight=about 8000), in an amount of 0.021 g ($1\times10^{-4}$ moles as anionic sites) were separately dissolved in 10 ml of distilled water (pH 8.0). The two aqueous solutions (5 ml, respectively) obtained were mixed together in a beaker to form a polyelectrolyte complex gel (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Further, 3 ml of the aqueous solution of the cationic polymer and 7 ml of the aqueous solution of the anionic polymer prepared in the same manner as above were mixed together in a beaker to form a polyelectrolyte complex gel (charge balance=−4).

Preparation Example 4: Preparation of PEC (PVBMA-CLA)

A cationic polymer, poly (vinylbenzyltrimethylammonium chloride) (PVBMA) (average molecular weight=about 100000), in an amount of 0.106 g ($5\times10^{-4}$ moles as cationic sites), and an anionic polymer, acrylic acid/lauryl acrylate random copolymer (CLA) (acrylic acid content=about 80 mole percent; average molecular weight=about 4000), in an amount of 0.090 g ($5\times10^{-4}$ moles as anionic sites) were separately dissolved in 10 ml of physiological saline solution (pH 7.4). The two aqueous solutions (5 ml, respectively) obtained were mixed together in a beaker to form a polyelectrolyte complex gel (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 5: Preparation of PEC (2X-Sodium Alginate)

A cationic polymer, poly[(dimethyliminio)ethylene-(dimethyliminio)-methylene-1,4-phenylenemethylene dichloride] (2X) (average molecular weight=about 6000), in an amount of 0.015 g ($1\times10^{-4}$ moles as cationic sites), and an anionic polysaccharide, sodium alginate (average molecular weight=about 500,000), in an amount of 0.020 g ($1\times10^{-4}$ moles as anionic sites) were separately dissolved in 10 ml of distilled water (pH 8.0). The two aqueous solutions (5 ml, respectively) obtained were mixed together in a beaker to form a polyelectrolyte complex gel (charge balance=±0).

Similarly, 0.075 g of the above-mentioned cationic polymer ($5\times10^{-4}$ moles as cationic sites) and 0.100 g of the polysaccharide ($5\times10^{-4}$ moles as anionic sites) were separately dissolved in 10 ml of distilled water (pH 8.0). The aqueous solution (7 ml) of the cationic polymer and the aqueous solution (3 ml) of the polysaccharide were mixed together in a beaker to form a polyelectrolyte complex gel (charge balance=+4).

Preparation Example 6: Preparation of PEC (PVBMA-Sodium Alginate)

A cationic polymer, poly (vinylbenzyltrimethylammonium chloride) (PVBMA) (average molecular weight=about 15,000), in an amount of 0.106 g ($5\times10^{-4}$ moles as cationic sites), and an anionic polysaccharide, sodium alginate (average molecular weight=about 100,000), in an amount of 0.100 g ($5\times10^{-4}$ moles as anionic sites) were separately dissolved in 10 ml of distilled water (pH 8.0). The two aqueous solutions (5 ml, respectively) obtained were mixed together in a beaker to form a polyelectrolyte complex gel (charge balance=±0).

The aqueous solution (7 ml) of the cationic polymer and the aqueous solution (3 ml) of the polysaccharide prepared in the same manner as above were mixed together in a beaker to form a polyelectrolyte complex gel (charge balance=+4).

Preparation Example 7: Preparation of PEC (2X-Polyglutamic Acid)

A cationic polymer, poly[(dimethyliminio)ethylene-(dimethyliminio)-methylene-1,4-phenylene methylene dichloride] (2X) (average molecular weight=about 6000), in an amount of 0.015 g ($1\times10^{-4}$ moles as cationic sites), and an anionic polymer, polyglutamic acid (PGA) (average molecular weight=about 4000), in an amount of 0.013 g ($1\times10^{-4}$ moles as anionic sites) were separately dissolved in 10 ml of physiological saline solution (pH 7.4). The two aqueous solutions (5 ml, respectively) obtained were mixed together in a beaker to form a polyelectrolyte complex gel [2X-PGA] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 8: Preparation of PEC (PVBMA-Aspartic Acid/Alanine Copolymer)

A cationic polymer, poly(vinylbenzyltrimethylammonium chloride) (PVBMA) (average molecular weight=about 15,000), in an amount of 0.106 g ($5\times10^{-4}$ moles as cationic sites), and an anionic polymer, aspartic acid/alanine random copolymer [C(Asp/Ala)] (aspartic acid content=about 65 mole percent, average molecular weight=about 8000), in an amount of 0.090 g ($5\times10^{-4}$ moles as anionic sites) were separately dissolved in 10 ml of distilled water (pH 9.0). The two aqueous solutions (5 ml, respectively) obtained were mixed together in a beaker at room temperature to form a polyelectrolyte complex gel [PVBMA-C(Asp/Ala)] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 9: Preparation of PEC [Poly (L-Lysine)-CLA)]

A cationic polymer, poly(L-lysine) (PLL) (average molecular weight=about 3000), in an amount of 1.3 mg ($1\times10^{-5}$ moles as cationic sites), and an anionic polymer, acrylic acid/lauryl acrylate random copolymer (CLA) (acrylic acid content=about 80 mole percent; average molecular weight=about 5000), in an amount of 1.8 mg ($1\times10^{-5}$ moles as anionic sites) were separately dissolved in 10 ml of an aqueous solution of 0.5 mole/liter sodium chloride (pH 6.5). The two aqueous solutions (5 ml, respectively) obtained were mixed together in a beaker at room temperature to form a polyelectrolyte complex gel [PLL-CLA] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 10: Preparation of PEC (Lysine/Serine Copolymer-Polyglutamic acid)

A cationic polymer, lysine/serine random copolymer [C(Lys/Ser)] (lysine content=about 70 mole percent, average molecular weight=about 10000), in an amount of 0.019 g ($1\times10^{-4}$ moles as cationic sites), and an anionic polymer, polyglutamic acid (PGA) (average molecular weight=about 2000), in an amount of 0.013 g ($1\times10^{-4}$ moles as anionic sites) were separately dissolved in 10 ml of physiological saline solution (pH 7.4). The two aqueous solutions (5 ml, respectively) obtained were mixed together in a beaker to form a polyelectrolyte complex gel [C(Lys/Ser)-PGA] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 11: Preparation of PEC [Poly (L-Lysine)-Sodium Alginate)

A cationic polymer, poly(L-lysine) (PLL) (average molecular weight=about 3000), in an amount of 1.3 mg ($1\times10^{-5}$ moles as cationic sites), and an anionic polymer, sodium alginate (Arg) (average molecular weight=about 40000), in an amount of 1.8 mg ($1\times10^{-5}$ moles as anionic sites) were separately dissolved in 10 ml of an aqueous solution of 0.5 mole/liter sodium chloride (pH 6.5). The two aqueous solutions (5 ml, respectively) obtained were mixed together in a beaker at room temperature to form a polyelectrolyte complex gel [PLL-Arg] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 12: Preparation of PEC (Lysine/Serine Copolymer-Carboxymethylchitin)

A cationic polymer, lysine/serine [C(lys/Ser)] random copolymer (lysine content=about 70 mole percent) (average molecular weight=about 10000), in an amount of 0.019 g ($1\times10^{-4}$ moles as cationic sites), and an anionic polymer, carboxymethylchitin (CM-Chn) (carboxymethylation degree=about 0.65/monosaccharide) (average molecular weight=about 5000), in an amount of 0.018 g ($1\times10^{-4}$ moles as anionic sites) were separately dissolved in 10 ml of a physiological saline solution (pH 7.4). The two aqueous solutions (5 ml, respectively) obtained were mixed together in a beaker at room temperature to form a polyelectrolyte complex gel [C(Lys/Ser)-CM-Chn] (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 13: Preparation of PEC (Chitosan-Sodium Alginate)

A cationic polysaccharide, chitosan (deacetylization degree=100 percent; average molecular weight=about 2000), in an amount of 0.020 g ($1\times10^{-4}$ moles as cationic sites), and an anionic polymer, sodium alginate (Arg) (average molecular weight=about 4000), in an amount of 0.018 g ($1\times10^{-4}$ moles as anionic sites) were separately dissolved in 10 ml of a physiological saline solution (pH 7.4). The two aqueous solutions (5 ml, respectively) obtained were mixed together in a beaker at room temperature to form a polyelectrolyte complex Gel (chitosan-Arg) (charge balance=±0).

The aqueous solution (7 ml) of the cationic polysaccharide and the aqueous solution (3 ml) of the anionic polymer prepared in the same manner as above were mixed together in a beaker to form a polyelectrolyte complex gel (charge balance=+4).

Preparation Example 14: Preparation of PEC (Chitosan-Sulfated Cellulose)

A cationic polysaccharide, chitosan (deacetylization degree=about 70 percent; average molecular weight=about 5000), in an amount of 0.102 g ($5 \times 10^{-4}$ moles as cationic sites), and an anionic polymer, sulfated cellulose (S-cel) (sulfation degree=about 0.8/monosaccharide; average molecular weight=about 8000), in an amount of 0.110 g ($5 \times 10^{-4}$ moles as anionic sites) were separately dissolved in 10 ml of distilled water (pH 5.0). The two aqueous solutions (5 ml, respectively) obtained were mixed together in a beaker at room temperature to form a polyelectrolyte complex gel (chitosan-S-cel) (charge balance=±0).

The aqueous solution (7 ml) of the cationic polysaccharide and the aqueous solution (3 ml) of the anionic polymer prepared in the same manner as above were mixed together in a beaker to form a polyelectrolyte complex gel (charge balance=+4).

Preparation Example 15: Preparation of PEC (Diethylaminoethyldextran-Carboxymethylchitin)

A cationic polysaccharide, diethylaminoethyldextran (DEAE-Dex) (rate of introduction=60 percent; average molecular weight=about 3000), in an amount of 2.0 mg ($1 \times 10^{-5}$ moles as cationic sites), and an anionic polymer, carboxymethylchitin (CM-Chn) (carboxymethylation degree=about 0.65/monosaccharide; average molecular weight=about 5000), in an amount of 1.8 mg ($1 \times 10^{-5}$ moles as anionic sites) were separately dissolved in 10 ml of an aqueous solution of 0.5 mole/liter sodium chloride (pH 8.0). The two aqueous solutions (5 ml, respectively) obtained were mixed together in a beaker at room temperature to form a polyelectrolyte complex gel (DEAE.Dex-CM-Chn) (charge balance=±0).

The aqueous solution (7 ml) of the cationic polysaccharide and the aqueous solution (3 ml) of the anionic polymer prepared in the same manner as above were mixed together in a beaker to form a polyelectrolyte complex gel (charge balance=+4).

Preparation Example 16: Preparation of PEC (Chitosan-Polyglutamic Acid)

A cationic polymer, chitosan (deacetylization degree=100 percent) (average molecular weight=about 2000), in an amount of 0.020 g ($1 \times 10^{-4}$ moles as cationic sites), and an anionic polymer, polyglutamic acid (PGA) (average molecular weight=about 4000), in an amount of 0.013 g ($1 \times 10^{-4}$ moles as anionic sites) were separately dissolved in 10 ml of a physiological saline solution (pH 7.4). The two aqueous solutions (5 ml, respectively) obtained were mixed together in a beaker at room temperature to form a polyelectrolyte complex gel (Chitosan-PGA) (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Preparation Example 17: Preparation of PEG (Chitsoan-CLA)

A cationic polymer, chitosan (deacetylization degree=70 percent) (average molecular weight=about 3000), in an amount of 0.021 g ($1 \times 10^{-4}$ moles as cationic sites), and an anionic polymer, acrylic acid/lauryl acrylate random copolymer (CLA) (acrylic acid content=about 80 molar percent) (average molecular weight=about 4000), in an amount of 0.018 g ($1 \times 10^{-4}$ moles as anionic sites) were separately dissolved in 10 ml of an aqueous solution of 0.3 mole/liter sodium chloride (pH 6.5). The two aqueous solutions (5 ml, respectively) obtained were mixed together in a beaker at room temperature to form a polyelectrolyte complex gel (Chitosan-CLA) (charge balance=±0).

The aqueous solution (7 ml) of the cationic polymer and the aqueous solution (3 ml) of the anionic polymer prepared in the same manner as above were mixed together in a beaker to form a polyelectrolyte complex gel (charge balance=+4).

Immobilization Example 1: Immobilization to Carrier (Polyethylene Tube)

Two ml amounts of the PEC gel liquids prepared in Preparation Examples 1 to 17 were poured into polyethylene tubes (inside diameter=1.0 cm) and rotated by a rotor at 60 rpm for 8 hours, respectively. After the PEC was coated on the inside walls of the polyethylene tubes, the supernatant was removed. The tubes were dried at 60° C. for 4 hours, washed the insides by 10 ml of distilled water three times, and then were again dried at 80° C. for 4 hours to obtain the PEC immobilized tubes.

Immobilization Example 2: Immobilization to Carrier (Gauze)

Pieces of cotton gauze (10 cm×10 cm) were immersed for 8 hours in the PEC gel liquids prepared in Preparation Examples 1 to 17. The gauze pieces were taken out therefrom, washed with 20 ml of distilled water, dried at 60° C. for 4 hours, then washed by 10 ml of distilled water three times, and dried at 80° C. for 4 hours to obtain the PEC immobilized gauze.

Immobilization Example 3: Immobilization to Carrier (Glass Beads)

Glass beads (diameter=0.2 mm; made by Toshiba Varotini K.K.) were immersed for 6 hours in the PEC gel liquids prepared in Preparation Examples 1 to 6. After the glass beads were coated by the PEC, the supernatant was removed. The beads were dried at 60° C. for 4 hours, washed by 10 ml of distilled water three times, and again dried at 80° C. for 4 hours to obtain PEC immobilized beads.

Immobilization Example 4: Immobilization to Carrier [Contact Lens Material (Polymethylmethacrylate)]

Small circular pieces (diameter=8 mm) punched out from polymethylmethacrylate sheets made of the material same as that for contact lenses (hereinafter referred to as "small circular pieces") were immersed at room temperature for 10 hours in the PEC gel liquids prepared in Preparation Examples 7 to 17. After the small circular pieces were coated by the PEC, the supernatant was removed. The pieces were dried at 60° C. for 3 hours, washed by 10 ml of distilled water twice and washed by physiological saline solutions twice, and then dried at 80° C. for 4 hours to obtain PEC immobilized small circular pieces.

Pharmacological Test Example 1: Examination of Antibacterial Property

The following microorganisms were used to examine the antibacterial property.

*Escherichia coli* ATCC25932
*Staphylococcus aureus* ATCC25923
*Serratia marcescens* IFO3046
*Pseudomonas aeruginosa* ATCC10145

The various bacterial solutions cultivated in brain heart infusion (BHI) media at 37° C. for 15 hours were diluted by an M/15 phosphate buffer solution (PBS, pH 6.8) containing 0.85% sodium chloride to prepare bacterial suspensions having a bacteria concentration of about $1\times10^4$/ml. After 10 ml of a PD medium (prepared by dissolving 7.0 g of dipotassium hydrogenphosphate, 2.0 g of potassium hydrogenphosphate, 0.1 g of magnesium sulfate, 1.0 g of ammonium sulfate, 0.5 g of sodium citrate, 10.0 g of glucose and 10.0 g of bactopeptone in 1000 ml of purified water) was added to the PEC-coated polyethylene tubes prepared in the above Immobilization Example 1, 0.1 ml of each of the above bacterial suspensions was added. The whole was mixed, and then held at 30° C. Shaking cultivation was carried out at 30° C. for 24 hours and the turbidity of the media was visually observed to examine the antibacterial effect. The results are shown in Table 1.

Pharmacological Test Example 2: Examination of Antibacterial Property

Fifty ml portions of a PD medium were inserted into Sakaguchi-flasks, then three pieces of the PEC-immobilized gauze (6 cm×6 cm) obtained in Immobilization Example 2 were introduced to the flasks, and 1 ml of the bacterial suspensions used in the above Pharmacological Test Example 1 were inoculated in an amount of about $1\times10^4$ bacteria. Further, inoculation was carried out in the same manner as above, in each of flasks for a blank test and those for a control test wherein three pieces of gauze (6 cm×6 cm) without immobilized-PEC were introduced. Then, shaking cultivation was carried out at 30° C. for 16 hours for each flask. The turbidity of the media was visually observed to examine the antibacterial effect. The results are shown in Table 2.

Pharmacological Test Example 3: Examination of Antibacterial Property

Ten ml portions of a PD medium were poured into sterilized polyethylene tubes, then 1 g of the PEC-immobilized glass beads obtained in immobilization Example 3 was introduced thereto and 0.1 ml of the bacterial suspensions as in the above-mentioned Pharmacological Test Example 1 was added. The whole was mixed and held at 30° C. Further, inoculation was carried out in the same manner as above, in each of tubes for a blank test and those for a control test wherein 1 g of glass beads without immobilized-PEC was introduced. Then, shaking cultivation was carried out at 30° C. for 24 hours for each tube. The turbidity of the media was visually observed to examine the antibacterial effect. The results are shown in Table 3.

Pharmacological Test Example 4: Examination of Antibacterial Property

Ten ml portions of a PD medium were poured into sterilized polyethylene tubes, then 2 g of the PEC-immobilized small circular pieces obtained in Immobilization Example 4 was added and 0.1 ml of the bacterial suspensions as in the above Pharmacological Test Example 1 was added. The whole was mixed and held at 30° C. Further, inoculation was carried out in the same manner as above, in each of tubes for a blank test and those for a control test wherein 2 g of the small circular pieces without immobilized-PEC was introduced. Then, shaking cultivation was carried out at 30° C. for 24 hours for each tube. The turbidity of the media was visually observed to examine the antibacterial effect. The results are shown in Table 4.

Pharmacological Test Example 5: Examination of Sustained Antibacterial Property Ten ml portions of purified water were added to PEC-immobilized tubes prepared in immobilization Example 1, then the tubes were vigorously shaken in a shaker for 2 minutes, and the washing solutions were discarded. The washing as above was repeated further four times (five times in total), and then the tubes were dried at 60° C. for 2 hours. The thus pre-treated tubes were used to examine the sustained antibacterial effect by the procedure as in Pharmacological Test Example 1 for *E. coli* (ATCC25932). The results are shown in Table 5.

Pharmacological Test Example 6: Examination of Sustained Antibacterial Property Pieces of PEC-immobilized gauze prepared in Immobilization Example 2 were introduced in 1000 ml beakers, 500 ml of purified water was added thereto, magnetic stirrers were used for agitation for 5 minutes, and then the washing solutions were discarded. The washing as above was repeated further four times (five times in total). Then, the pieces of gauze were taken out therefrom and dried at 60° C. for 4 hours. The thus pre-treated pieces of gauze were used to examine the sustained antibacterial effect by the procedure as in Pharmacological Test Example 2 for *E. coli* (ATCC25932). The results are shown in Table 6.

Pharmacological Test Example 7: Examination of Sustained Antibacterial Property PEC-immobilized glass beads prepared in Immobilization Example 3 were placed in sterilized polyethylene tubes, 10 ml of purified water was added, then the tubes were vigorously shaken in a shaker for 2 minutes, and then the washing solutions were discarded. The washing as above was repeated further four times (five times in total), then the glass beads were taken out therefrom and were dried at 60° C. for 4 hours. The thus pretreated glass tubes were used to examine the sustained antibacterial effect by the procedure as in Pharmacological Test Example 3 for *E. coli* (ATCC25932). The results are shown in Table 7.

Pharmacological Test Example 8: Examination of Sustained Antibacterial Property PEC-immobilized small circular pieces prepared in Immobilization Example 4 were introduced into sterilized polyethylene tubes, 10 ml of purified water was added, then the tubes were vigorously shaken in a shaker for 2 minutes, then the washing solutions were discarded. The washing as above was repeated further four times (five times in total), then the small circular pieces were taken out therefrom and dried at 60° C. for 4 hours. The thus pretreated small circular pieces were used to examine the sustained antibacterial effect by the procedure as in Pharmacological Test Example 4 for *E. coli* (ATCC25932). The results are shown in Table 8.

Pharmacological Test Example 9: Examination of Antibacterial Property

Pieces of filter paper (TOYO, No. 5B) were immersed for 8 hours in the PEC gel solutions prepared in Preparation Examples 1 to 17. The pieces of filter paper were taken out therefrom and washed with 20 ml of distilled water, then dried at 60° C. for 4 hours, further washed by 10 ml of distilled water three times, and dried at 80° C. for 4 hours. The resulting filter paper pieces were cut into circular pieces having a diameter of 13 mm and subjected to gas sterilization treatment to obtain the test disks for antibacterial effect as below. Further, the same procedure was repeated, except that the circular filter paper not immersed in PEC gel solutions was used, to prepare control disks.

The four types of bacteria described in Pharmacological Test Example 1 were shake-cultivated overnight in BHI media by the same method as in Pharmacological Test Example 1 and subjected to three centrifugation treatments by the BHI media, then diluted by BHI media to prepare bacterial suspensions having a bacteria concentration of about $1\times10^7$/ml. Twenty μl portions of the bacterial suspensions were inoculated in the above antibacterial effect test disks and control disks. The disks were allowed to stand at 37° C. for 2 hours, then placed on Trypto-soya agar plates so that the inoculated sides of the disks contacted the agar plates. The whole was allowed to stand at 37° C. for 1 hour, then the disks were removed. The plates were incubated at 37° C. overnight, then the formation of colonies on the plate was observed. The results are shown in Table 9.

EXAMPLES 1 TO 11

Various types of PEC were prepared in the same manner as in the above-mentioned preparation examples and immobilized on carriers, and then, the pharmacological activities were observed. More particularly, the cationic polymers shown in Table 10 and the anionic polymers shown in Table 11 were dissolved in the amounts shown in the "Amount taken" columns of Tables 10 and 11 in 10 ml of the solvents shown in the "Solvent" column of Table 10. The obtained solutions (5 ml, respectively) were mixed all at once in a beaker to form a polyelectrolyte complex gel (charge balance=±0). Similarly, polyelectrolyte complex gels having a charge balance of +4 or −4 were formed from 7 ml of the cationic polymer solutions and 3 ml of the anionic polymer solutions, or from 7 ml of the anionic polymer solutions and 3 ml of the cationic polymer solutions. The resulting PEC gels were immobilized on carriers (gauze) by the same method as in immobilization Example 2 and the antibacterial properties were observed by the same method as in Pharmacological Test Example 2. The results are shown in Table 12. It is noted that in Tables 10 and 11, the polymers are shown by abbreviations. The meanings of the abbreviations are as follows (the abbreviations used in the above Preparation Examples have the same meanings, so the explanations thereabout are omitted).

6X: Poly[(dimethyliminio)hexamethylene(dimethyliminio)-methylene-1,4-phenylenemethylene dichloride]
PAA: Polyacrylic acid
PSS: Polystyrenesulfonic acid
SLA65: Styrenesulfonic acid/laurylacrylate random copolymer (styrene sulfonic acid content=about 65 mole percent)
CSA74: Acrylic acid/stearylacrylate random copolymer (acrylic acid content=about 74 mole percent)
CLA66: Acrylic acid/laurylacrylate random copolymer (acrylic acid content=about 66 mole percent)
QPA1-Am: Quaternized polyallylamine In the following Tables 1 to 8 and 12, the symbols have the following meanings:
+++: strong turbidity
++: turbidity
+: a little turbidity
±: no change
−: transparent.

TABLE 1

| PEC | Charge balance | E. coli | S. aureus | S. marce-scens | P. aerugi-nosa |
|---|---|---|---|---|---|
| 2X-CLA | ±0 | − | − | − | ± |
|  | +4 | − | − | − | − |
|  | −4 | ++ | ++ | +++ | +++ |
| 2X-COA | ±0 | + | ++ | +++ | +++ |
|  | +4 | − | − | − | ± |
|  | −4 | ++ | ++ | +++ | +++ |
| PVBMA-COA | ±0 | − | − | ++ | ++ |
|  | +4 | − | − | + | ++ |
|  | −4 | ++ | ++ | +++ | +++ |
| PVBMA-CLA | ±0 | + | + | ++ | ++ |
|  | +4 | ++ | ++ | ++ | ++ |
| 2X-alginic acid | ±0 | − | − | − | − |
|  | +4 | − | − | − | − |
| PVBMA-alginic acid | ±0 | − | − | + | + |
|  | +4 | ± | − | ++ | ++ |
| 2X-PGA | ±0 | + | + | + | + |
|  | +4 | − | − | ± | ± |
| PVBMA-C(Asp/Ala) | ±0 | ± | + | + | ± |
|  | −4 | − | − | ± | ± |
| PLL-CLA | ±0 | − | − | − | − |
|  | +4 | − | − | − | − |
| C(Lys/Ser)-PGA | ±0 | + | ++ | ++ | ++ |
|  | +4 | ± | − | − | − |
| PLL-Arg | ±0 | − | ± | ± | + |
|  | +4 | − | − | − | ± |
| C(Lys/Ser)-CM-chn | ±0 | ± | + | + | + |
|  | +4 | − | ± | − | ± |
| Chitosan-Arg | ±0 | + | + | + | + |
|  | +4 | − | − | ± | ± |
| Chitosan-S.cel | ±0 | ± | ± | ± | ± |
|  | +4 | − | − | − | − |
| DEAE.Dex-CM.Chn | ±0 | − | − | − | − |
|  | +4 | − | − | − | − |
| Chitosan-PGA | ±0 | + | + | ± | + |
|  | +4 | − | − | − | ± |
| Chitosan-CLA | ±0 | + | + | + | + |
|  | +4 | − | − | ± | ± |
| Blank test |  | ++ | ++ | +++ | +++ |

TABLE 2

| PEC | Charge balance | E. coli | S. aureus | S. marce-scens | P. aerugi-nosa |
|---|---|---|---|---|---|
| 2X-CLA | ±0 | − | − | + | + |
|  | +4 | − | − | − | − |
|  | −4 | ++ | ++ | +++ | +++ |
| 2X-COA | ±0 | ++ | ++ | ++ | ++ |
|  | +4 | − | − | ± | + |
|  | −4 | ++ | ++ | +++ | +++ |
| PVBMA-COA | ±0 | − | − | ++ | ++ |
|  | +4 | ± | ± | ++ | +++ |
|  | −4 | + | + | ++ | +++ |
| PVBMA-CLA | ±0 | ± | ± | +++ | +++ |
|  | +4 | + | ++ | +++ | +++ |
| 2X-alginic acid | ±0 | − | − | − | − |
|  | +4 | − | − | − | − |
| PVBMA-alginic acid | ±0 | − | − | + | ++ |
|  | +4 | ± | ± | ++ | ++ |
| 2X-PGA | ±0 | + | + | + | + |
|  | +4 | − | − | ± | ± |

TABLE 2-continued

| PEC | Charge balance | E. coli | S. aureus | S. marcescens | P. aeruginosa |
|---|---|---|---|---|---|
| PVBMA-C(Asp/Ala) | ±0 | + | + | + | ± |
|  | +4 | − | − | ± | ± |
| PLL-CLA | ±0 | − | − | − | − |
|  | +4 | − | − | − | − |
| C(Lys/Ser)-PGA | ±0 | + | ++ | ++ | ++ |
|  | +4 | ± | − | − | − |
| PLL - Arg | ±0 | − | ± | ± | + |
|  | +4 | − | − | − | ± |
| C(Lys/Ser)-CM-chn | ±0 | ± | + | + | + |
|  | +4 | − | ± | − | ± |
| Chitosan-Arg | ±0 | + | + | + | + |
|  | +4 | − | − | ± | ± |
| Chitosan-S.cel | ±0 | ± | ± | ± | ± |
|  | +4 | − | − | − | − |
| DEAE.Dex-CM.Chn | ±0 | − | − | − | − |
|  | +4 | − | − | − | − |
| Chitosan-PGA | ±0 | + | + | ± | + |
|  | +4 | − | − | − | ± |
| Chitosan-CLA | ±0 | + | + | + | + |
|  | +4 | − | − | ± | ± |
| Blank test |  | ++ | ++ | +++ | +++ |
| Gauze alone |  | ++ | ++ | +++ | +++ |

TABLE 3

| PEC | Charge balance | E. coli | S. aureus | S. marcescens | P. aeruginosa |
|---|---|---|---|---|---|
| 2X-CLA | ±0 | − | − | + | + |
|  | +4 | − | − | − | − |
|  | −4 | ++ | ++ | +++ | +++ |
| 2X-COA | ±0 | ++ | ++ | ++ | ++ |
|  | +4 | − | − | ± | + |
|  | −4 | ++ | ++ | +++ | +++ |
| PVBMA-COA | ±0 | − | − | ++ | ++ |
|  | +4 | ± | ± | ++ | +++ |
|  | −4 | + | + | ++ | +++ |
| PVBMA-CLA | ±0 | ± | ± | +++ | +++ |
|  | +4 | + | ++ | +++ | +++ |
| 2X-alginic acid | +0 | − | − | − | − |
|  | +4 | − | − | − | − |
| PVBMA-alginic acid | ±0 | − | − | + | ++ |
|  | +4 | ± | ± | ++ | ++ |
| Blank test |  | ++ | ++ | +++ | +++ |
| Beads alone |  | ++ | ++ | +++ | +++ |

TABLE 4

| PEC | Charge balance | E. coli | S. aureus | S. marcescens | P. aeruginosa |
|---|---|---|---|---|---|
| 2X-PGA | ±0 | + | + | + | + |
|  | +4 | − | − | ± | ± |
| PVBMA-C(Asp/Ala) | ±0 | ± | + | + | ± |
|  | +4 | − | − | ± | ± |
| PLL-CLA | ±0 | − | − | − | − |
|  | +4 | − | − | − | − |
| C(Lys/Ser)-PGA | ±0 | + | ++ | ++ | ++ |
|  | +4 | ± | − | − | − |
| PLL - Arg | ±0 | − | ± | ± | + |
|  | +4 | − | − | − | ± |
| C(Lys/Ser)-CM - chn | ±0 | ± | + | + | + |
|  | +4 | − | ± | − | ± |
| Chitosan-Arg | ±0 | + | + | + | + |
|  | +4 | − | − | ± | ± |
| Chitosan-S.cel | ±0 | ± | ± | ± | ± |
|  | +4 | − | − | − | − |
| DEAE.Dex-CM.Chn | ±0 | − | − | − | − |
|  | +4 | − | − | − | − |
| Chitosan-PGA | ±0 | + | + | ± | + |

TABLE 4-continued

| PEC | Charge balance | E. coli | S. aureus | S. marcescens | P. aeruginosa |
|---|---|---|---|---|---|
| PGA | +4 | − | − | − | ± |
| Chitosan-CLA | ±0 | + | + | + | + |
|  | +4 | − | − | ± | ± |
| Blank test |  | ++ | ++ | +++ | +++ |
| Small circular pieces alone |  | ++ | ++ | +++ | +++ |

TABLE 5

| PEC | Charge balance | E. coli |
|---|---|---|
| 2X-CLA | ±4 | − |
|  | +4 | − |
|  | −4 | ++ |
| 2X-COA | ±0 | + |
|  | +4 | − |
|  | −4 | ++ |
| PVBMA-COA | ±0 | − |
|  | +4 | − |
|  | −4 | ++ |
| PVBMA-CLA | ±0 | + |
|  | +4 | ++ |
| 2X-alginic acid | ±0 | − |
|  | +4 | − |
| PVBMA-alginic acid | ±0 | − |
|  | +4 | ± |
| 2X-PGA | ±0 | + |
|  | +4 | − |
| PVBMA-C(Asp/Ala) | ±0 | ± |
|  | +4 | − |
| PLL-CLA | ±0 | − |
|  | +4 | − |
| C(Lys/Ser)-CM - chn PGA | ±0 | ± |
|  | +4 | − |
| PLL-Arg | ±0 | − |
|  | +4 | − |
| C(Lys/Ser)- | ±0 | ± |
|  | +4 | − |
| Chitosan-Arg | ±0 | + |
|  | +4 | − |
| Chitosan-S.cel | ±0 | ± |
|  | +4 | − |
| DEAE.Dex-CM.Chn | ±0 | − |
|  | +4 | − |
| Chitosan-PGA | ±0 | + |
|  | +4 | − |
| Chitosan-CLA | ±0 | + |
|  | +4 | − |
| Blank test |  | ++ |

TABLE 6

| PEC | Charge balance | E. coli |
|---|---|---|
| 2X-CLA | ±0 | − |
|  | +4 | − |
|  | −4 | ++ |
| 2X-COA | ±0 | ++ |
|  | +4 | − |
|  | −4 | ++ |
| PVBMA-COA | ±0 | − |
|  | +4 | ± |
|  | −4 | + |
| PVBMA-CLA | ±0 | ± |
|  | +4 | + |
| 2X-alginic acid | ±0 | − |
|  | +4 | − |
| PVBMA-alginic acid | ±0 | − |
|  | +4 | ± |
| 2X-PGA | ±0 | + |

TABLE 6-continued

| PEC | Charge balance | E. coli |
|---|---|---|
| | +4 | − |
| PVBMA-C(Asp/Ala) | ±0 | ± |
| | +4 | − |
| PLL-CLA | ±0 | − |
| | +4 | − |
| C(Lys/Ser)-PGA | ±0 | + |
| | +4 | ± |
| PLL-Arg | ±0 | − |
| | +4 | − |
| C(Lys/Ser)-CM-chn | ±0 | ± |
| | +4 | − |
| Chitosan-Arg | ±0 | + |
| | +4 | − |
| Chitosan-S.cel | ±0 | ± |
| | +4 | − |
| DEAE.Dex-CM.Chn | ±0 | − |
| | +4 | − |
| Chitosan-PGA | ±0 | + |
| | +4 | − |
| Chitosan-CLA | ±0 | + |
| | +4 | − |
| Blank test | | ++ |
| Gauze alone | | ++ |

TABLE 7

| PEC | Charge balance | E. coli |
|---|---|---|
| 2X-CLA | ±0 | − |
| | +4 | − |
| | −4 | ++ |
| 2X-COA | ±0 | ++ |
| | +4 | − |
| | −4 | ++ |
| PVBMA-COA | ±0 | − |
| | +4 | ± |
| | −4 | + |
| PVBMA-CLA | ±0 | ± |
| | +4 | + |
| 2X-alginic acid | ±0 | − |
| | +4 | − |
| PVBMA-alginic acid | ±0 | − |
| | +4 | ± |
| Blank test | | ++ |
| Beads alone | | ++ |

TABLE 8

| PEC | Charge balance | E. coli |
|---|---|---|
| 2X-PGA | ±0 | + |
| | +4 | − |
| | ±0 | − |
| PVBMA-C(Asp/Ala) | ±0 | ± |
| | +4 | − |
| PLL-CLA | ±0 | − |
| | +4 | − |
| C(Lys/Ser)-PGA | ±0 | ± |
| | +4 | − |
| PLL-Arg | ±0 | − |
| | +4 | − |
| C(Lys/Ser)-CM-chn | ±0 | ± |
| | +4 | − |
| Chitosan-Arg | ±0 | + |
| | +4 | − |
| Chitosan-S.cel | ±0 | ± |
| | +4 | − |
| DEAE.Dex-CM.Chn | ±0 | − |
| | +4 | − |
| Chitosan-PGA | ±0 | + |
| | +4 | − |
| Chitosan- | ±0 | + |

TABLE 8-continued

| PEC | Charge balance | E. coli |
|---|---|---|
| CLA | +4 | − |
| Blank test | | ++ |
| Small circular pieces alone | | ++ |

In the following Table 9, the symbols show the degree of colony formation. The degrees are as follows:

+++: Great
++: Medium
+: Small
±: Extremely small
−: No change

TABLE 9

| PEC | Charge balance | E. coli | S. aureus | S. marcescens | P. aeruginosa |
|---|---|---|---|---|---|
| 2X-CLA | ±0 | − | − | + | ++ |
| | +4 | ± | − | ± | + |
| | −4 | ++ | ++ | +++ | +++ |
| 2X-COA | ±0 | ++ | ++ | ++ | ++ |
| | +4 | − | ± | + | ++ |
| | −4 | ++ | ++ | +++ | +++ |
| PVBMA-COA | ±0 | − | − | ++ | ++ |
| | +4 | ± | ± | + | ++ |
| | −4 | + | + | ++ | +++ |
| PVBMA-CLA | ±0 | + | + | +++ | ++ |
| | +4 | + | ++ | +++ | +++ |
| 2X-alginic acid | ±0 | − | − | − | ± |
| | +4 | − | − | − | ± |
| PVBMA-alginic acid | ±0 | − | − | ± | ++ |
| | +4 | ± | − | − | ++ |
| 2X-PGA | ±0 | + | + | + | + |
| | +4 | − | − | ± | ± |
| PVBMA-C(Asp/Ala) | ±0 | ± | + | + | ± |
| | +4 | − | − | ± | ± |
| PLL-CLA | ±0 | − | − | − | − |
| | +4 | − | − | − | − |
| C(Lys/Ser)-PGA | ±0 | ± | ± | ± | ± |
| | +4 | − | − | − | − |
| PLL-Arg | ±0 | − | ± | ± | + |
| | +4 | − | − | − | ± |
| C(Lys/Ser)-CM-chn | ±0 | ± | + | + | + |
| | +4 | − | ± | − | ± |
| Chitosan-Arg | ±0 | + | + | + | + |
| | +4 | − | − | − | ± |
| Chitosan-S.cel | ±0 | ± | ± | ± | ± |
| | +4 | − | − | − | − |
| DEAE.Dex-CM.Chn | ±0 | − | − | ± | ± |
| | +4 | − | − | − | − |
| Chitosan-PGA | ±0 | + | + | ± | + |
| | +4 | − | − | − | ± |
| Chitosan-CLA | ±0 | + | + | + | + |
| | +4 | − | − | ± | ± |
| Control | | +++ | +++ | +++ | +++ |

TABLE 10

| Ex. | Cationic polymer | Average molecular weight | Amount taken (g) | Cationic sites (moles) | Solvent |
|---|---|---|---|---|---|
| 1 | 6X | 12000 | 0.020 | $1 \times 10^{-4}$ | Distilled water (pH 8.5) |
| 2 | 2X | 8000 | 0.007 | $5 \times 10^{-5}$ | Distilled water (pH 9.0) |
| 3 | 2X | 20000 | 0.0015 | $1 \times 10^{-5}$ | 0.5 M sodium chloride solution (pH 5.0) |

TABLE 10-continued

| Ex. | Cationic polymer | Average molecular weight | Amount taken (g) | Cationic sites (moles) | Solvent |
|---|---|---|---|---|---|
| 4 | 2X | 6000 | 0.015 | $1 \times 10^{-4}$ | Distilled water (pH 7.0) |
| 5 | 6X | 12000 | 0.201 | $1 \times 10^{-3}$ | 0.2 M sodium chloride solution (pH 6.5) |
| 6 | QPA1.Am | 13600 | 0.013 | $1 \times 10^{-4}$ | Distilled water (pH 8.0) |
| 7 | 2X | 6000 | 0.015 | $1 \times 10^{-4}$ | Distilled water (pH 6.0) |
| 8 | 6X | 6000 | 0.020 | $1 \times 10^{-4}$ | 0.8 M sodium chloride solution (pH 4.5) |
| 9 | 6X | 10000 | 0.010 | $5 \times 10^{-5}$ | Distilled water (pH 10.0) |
| 10 | 6X | 10000 | 0.020 | $1 \times 10^{-4}$ | Distilled water (pH 9.0) |
| 11 | Chitosan | 4000 | 0.008 | $5 \times 10^{-5}$ | Distilled water (pH 7.2) |

TABLE 11

| Ex. | Anionic polymer | Average molecular weight | Amount taken (g) | Anionic sites (moles) |
|---|---|---|---|---|
| 1 | CLA66 | 15000 | 0.021 | $1 \times 10^{-4}$ |
| 2 | PAA | 35000 | 0.005 | $5 \times 10^{-5}$ |
| 3 | PSS | 40000 | 0.0021 | $5 \times 10^{-5}$ |
| 4 | Phosphated chitin | 7000 | 0.032 | $1 \times 10^{-4}$ |
| 5 | Chondroitin sulfuric acid type A | 23000 | 0.460 | $1 \times 10^{-3}$ |
| 6 | Sodium alginate | 500000 | 0.040 | $1 \times 10^{-4}$ |
| 7 | Phosphated cellulose | 23000 | 0.029 | $1 \times 10^{-4}$ |
| 8 | SLA65 | 15000 | 0.031 | $1 \times 10^{-4}$ |
| 9 | CSA74 | 10800 | 0.011 | $5 \times 10^{-5}$ |
| 10 | Carboxymethy-cellulose (substitution degree 100) | 22000 | 0.022 | $1 \times 10^{-4}$ |
| 11 | Carboxymethyl cellulose (substitution degree 90) | 23000 | 0.012 | $5 \times 10^{-5}$ |

TABLE 12

| PEC | Charge balance | E. coli | S. aureus | S. marcescens | P. aeruginosa |
|---|---|---|---|---|---|
| 6X-CLA66 | −4 | + | ± | ± | + |
|  | ±0 | − | − | − | − |
|  | +4 | − | − | − | − |
| 2X-PPA | −4 | + | + | ++ | ++ |
|  | ±0 | − | − | − | − |
|  | +4 | − | − | − | − |
| 2X-PSS | ±0 | ++ | ++ | +++ | +++ |
|  | +4 | + | ± | + | + |
| 2X-phosphated chitin | −4 | + | + | ++ | ++ |
|  | ±0 | ± | ± | ± | ± |
|  | +4 | − | − | − | − |
| 6X-chondroitin sulfuric acid type A | −4 | + | + | +++ | +++ |
|  | ±0 | − | − | ++ | + |
|  | +4 | − | − | ± | ± |
| QPA1.Am-sodium | −4 | + | + | ++ | ++ |
|  | ±0 | − | − | + | ± |
| alginate | +4 | − | − | − | − |
| 2X-phosphated cellulose | −4 | + | + | ++ | ++ |
|  | ±0 | − | − | − | − |
|  | +4 | − | − | − | − |
| 6X-SLA65 | −4 | + | + | ++ | +++ |
|  | ±0 | + | + | ± | + |
|  | +4 | + | + | + | + |
| X-CSA74 | −4 | ± | ± | ± | + |
|  | ±0 | − | − | − | − |
|  | +4 | − | − | − | − |
| 6X-carboxymethyl-cellulose (substitution degree 100) | −4 | ± | ++ | ++ | ++ |
|  | ±0 | − | ± | − | − |
|  | +4 | − | − | − | − |
| Chitosan-carboxymethyl-cellulose (substitution degree 90) | −4 | + | + | +++ | +++ |
|  | ±0 | − | ± | + | + |
|  | +4 | − | − | − | − |
| Control |  | ++ | ++ | +++ | +++ |

INDUSTRIAL APPLICABILITY

The antibacterial agent according to the present invention can be applied to a wide range usage, because of insolubility in general solvents. Further, the antibacterial activity can be maintained for a long period of time. Still further, various antibacterial agents exhibiting various antibacterial strengths can be easily provided.

We claim:

1. An antibacterial agent containing a polyelectrolyte complex prepared by reacting a cationic polymer of the formula (I):

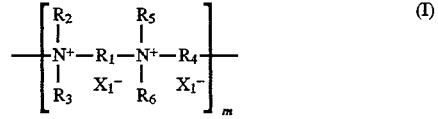

wherein $R_1$ and $R_4$ are, independently, an alkylene group of 1 to 10 carbon atoms, a group of the general formula:

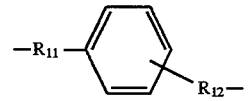

wherein $R_{11}$ and $R_{12}$ are, independently, an alkylene group of 1 or 2 carbon atoms, or an arylene group, and $R_2$, $R_3$, $R_5$ and $R_6$ are, independently, an alkyl group of 1 to 3 carbon atoms, or $R_1$ forms, together with the 2 nitrogen atoms and $R_2$, $R_3$, $R_5$ and $R_6$ in the formula, a group of the formula:

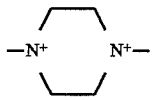

$R_4$ has the same meaning as above, $X_1^-$ is a counter ion, and m is a number of not less than 5, with an anionic polymer of the formula (V)

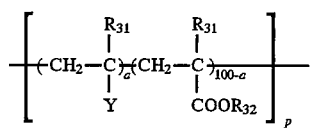 (V)

wherein $R_{31}$ is a hydrogen atom or a methyl group, $R_{32}$ is an alkyl group of 6 to 18 carbon atoms, Y is a group of a carboxylic acid or a salt thereof, a sulfonic acid or a salt thereof or a phosphoric acid or a salt thereof, or an aryl group containing a group of a carboxylic acid or a salt thereof, a sulfonic acid or a salt thereof or a phosphoric acid or a salt thereof, a is 20 to 100, and p is an integer of not less than 10, wherein the concentration ratio of cationic sites of the cationic polymer and anionic sites of the anionic polymer are within the range of 0.25 to 4.0 and recovering a reaction product of said cationic and anionic polymers.

2. An antibacterial agent according to claim 1 wherein, in formula (I), $R_1$ and $R_4$ are independently, a straight or branched alkylene group of 2 to 8 carbon atoms and $R_{11}$ and $R_{12}$ are bonded at the p-position.

3. An antibacterial material comprised of an antibacterially effective amount of the antibacterial agent of claim 2 and a carrier.

4. An antibacterial agent according to claim 1 wherein in formula (V) $R_{32}$ is a straight or branched alkyl group of 6 to 14 carbon atoms, and a is 50 to 100.

5. An antibacterial material comprised of an antibacterially effective amount of the antibacterial agent of claim 4 and a carrier.

6. An antibacterial material comprised of an antibacterially effective amount of the antibacterial agent of claim 1 and a carrier.

* * * * *